US009259415B2

(12) United States Patent
McDowell et al.

(10) Patent No.: US 9,259,415 B2
(45) Date of Patent: Feb. 16, 2016

(54) EFFICACY IN TREATING BACTERIAL INFECTIONS

(71) Applicants: Susan A. McDowell, Yorktown, IN (US); Robert E. Sammelson, Muncie, IN (US); Larry A. Sklar, Albuquerque, NM (US); Mark K. Haynes, Albuquerque, NM (US)

(72) Inventors: Susan A. McDowell, Yorktown, IN (US); Robert E. Sammelson, Muncie, IN (US); Larry A. Sklar, Albuquerque, NM (US); Mark K. Haynes, Albuquerque, NM (US)

(73) Assignees: Ball State Innovation Corporation, Muncie, IN (US); STC.UNM, Albuquerque, NM (US)

( * ) Notice: Subject to any disclaimer, the term of this patent is extended or adjusted under 35 U.S.C. 154(b) by 173 days.

(21) Appl. No.: 13/773,871

(22) Filed: Feb. 22, 2013

(65) Prior Publication Data

US 2013/0217744 A1 Aug. 22, 2013

Related U.S. Application Data

(60) Provisional application No. 61/601,807, filed on Feb. 22, 2012, provisional application No. 61/644,798, filed on May 9, 2012, provisional application No. 61/671,054, filed on Jul. 12, 2012.

(51) Int. Cl.
*A61K 31/415* (2006.01)
*A61K 31/63* (2006.01)
*A61K 31/635* (2006.01)

(52) U.S. Cl.
CPC .............. *A61K 31/415* (2013.01); *A61K 31/63* (2013.01); *A61K 31/635* (2013.01)

(58) Field of Classification Search
None
See application file for complete search history.

(56) References Cited

U.S. PATENT DOCUMENTS

2007/0066651 A1* 3/2007 Altisen et al. .................. 514/314
2013/0345277 A1* 12/2013 Wandinger-Ness et al. .. 514/403

OTHER PUBLICATIONS

Soong et al. (J. Biol. Chem., 286: 35891-35898, Aug. 2011).*
Wilding, E. I., D. Y. Kim, A. P. Bryant, M. N. Gwynn, R. D. Lunsford, D. McDevitt, J. E. Myers, Jr., M. Rosenberg, D. Sylvester, C. V. Stauffacher, and V. W. Rodwell. 2000. Essentiality, expression, and characterization of the class II 3-hydroxy-3-methylglutaryl coenzyme A reductase of *Staphylococcus aureus*. J Bacteriol 182(18):5147-52.
Jerwood, S., and J. Cohen. 2008. Unexpected antimicrobial effect of statins. J Antimicrob Chemother 61(2):362-4.
Lopez, D., and R. Kolter. 2010. Functional microdomains in bacterial membranes. Genes & Development 24 (17):1893-902.
Singh, R., P. Ray, A. Das, and M. Sharma. 2010. Enhanced production of exopolysaccharide matrix and biofilm by a menadione-auxotrophic *Staphylococcus aureus* small-colony variant. Journal of Medical Microbiology 59(Pt 5):521-7.
Que, Y. A., and P. Moreillon. 2011. Infective endocarditis. Nat Rev Cardiol 8(6):322-36.
Secor, P. R., G. A. James, P. Fleckman, J. E. Olerud, K. McInnerney, and P. S. Stewart. 2011. *Staphylococcus aureus* Biofilm and Planktonic cultures differentially impact gene expression, mapk phosphorylation, and cytokine production in human keratinocytes. BMC Microbiology 11:143.
Vanhaesebroeck, B., and M. D. Waterfield. 1999. Signaling by distinct classes of phosphoinositide 3-kinases. Exp Cell Res 253(1):239-54.
Cantley, L. C. 2002. The phosphoinositide 3-kinase pathway. Science 296(5573):1655-7.
Jimenez, C., R. A. Portela, M. Mellado, J. M. Rodriguez-Frade, J. Collard, A. Serrano, A. C. Martinez, J. Avila, and A. C. Carrera. 2000. Role of the PI3K regulatory subunit in the control of actin organization and cell migration. J Cell Biol 151(2):249-62.
Kim do, Y., K. H. Kim, N. D. Kim, K. Y. Lee, C. K. Han, J. H. Yoon, S. K. Moon, S. S. Lee, and B. L. Seong. 2006. Design and biological evaluation of novel tubulin inhibitors as antimitotic agents using a pharmacophore binding model with tubulin. Journal of Medicinal Chemistry 49(19):5664-70.
Bashir, R., S. Ovais, S. Yaseen, H. Hamid, M. S. Alam, M. Samim, S. Singh, and K. Javed. 2011. Synthesis of some new 1,3,5-trisubstituted pyrazolines bearing benzene sulfonamide as anticancer and anti-inflammatory agents. Bioorganic & Medicinal Chemistry Letters 21(14):4301-5.
Soliman, R. 1979. Preparation and antidiabetic activity of some sulfonylurea derivatives of 3,5-disubstituted pyrazoles. Journal of Medicinal Chemistry 22(3):321-5.
Yan, Q., R. Cao, W. Yi, Z. Chen, H. Wen, L. Ma, and H. Song. 2009. Inhibitory effects of 5-benzylidene barbiturate derivatives on mushroom tyrosinase and their antibacterial activities. European Journal of Medicinal Chemistry 44 (10):4235-43.
Knop, K., R. Hoogenboom, D. Fischer, and U. S. Schubert. 2010. Poly(ethylene glycol) in drug delivery: pros and cons as well as potential alternatives. Angew Chem Int Ed Engl 49(36):6288-308.
Gajbhiye, V., P. Vijayaraj Kumar, R. Kumar Tekade, and N. K. Jain. 2007. Pharmaceutical and biomedical potential of PEGylated dendrimers. Curr Pharm Design 13(4):415-29.
Seedher, N.,and S. Bhatia. Solubility enhancement of Cox-2 inhibitors using various solvent systems, AAPS PharmSciTech. 4 (2003) E33.
Klein, I.K., Preduscu, D.N., Sharma, T., Knezevic, I., Malik, A.B., et al. (2009) Intersectin-2L regulates caveola endocytosis secondary to CDC42—mediated actin polymerization. J Biol Chem 248: 25953-25961.
David, M. Z., and R. S. Daum. 2010. Community-associated methicillin-resistant *Staphylococcus aureus*: epidemiology and clinical consequences of an emerging epidemic. Clinical Microbiology Reviews 23(3):616-87.
Furuya, E. Y., and F. D. Lowy. 2003. Antimicrobial strategies for the prevention and treatment of cardiovascular infections. Current Opinion in Pharmacology 3(5):464-9.

(Continued)

*Primary Examiner* — Bong-Sook Baek
(74) *Attorney, Agent, or Firm* — Daniel L. Boots; Brian W. Chellgren; Bingham Greenebaum Doll LLP

(57) ABSTRACT

The present disclosure relates to molecules which function as selective modulators (i.e., inhibitors and agonists) of the Ras-homologous (Rho) family of small GTPases and, in particular, CDC42 GTPase, and their use to treat bacterial infection including systemic infection from sources such as *Staphylococcus aureus*.

18 Claims, 15 Drawing Sheets

(56) References Cited

OTHER PUBLICATIONS

Darouiche, R. O. 2004. Treatment of infections associated with surgical implants. N Engl J Med 350(14):1422-9.
Lowy, F. D. 1998. *Staphylococcus aureus* infections. N Engl J Med 339(8):520-32.
Otto, M. 2010. Looking toward basic science for potential drug discovery targets against community-associated MRSA. Medicinal Research Reviews 30(1):1-22.
Liappis, A. P., V. L. Kan, C. G. Rochester, and G. L. Simon. 2001. The effect of statins on mortality in patients with bacteremia. Clin Infect Dis 33(8):1352-7.
Almog, Y., A. Shefer, V. Novack, N. Maimon, L. Barski, M. Eizinger, M. Friger, L. Zeller, and A. Danon. 2004. Prior statin therapy is associated with a decreased rate of severe sepsis. Circulation 110(7):880-5.
Yasuda, H., P. S. Yuen, X. Hu, H. Zhou, and R. A. Star. 2006. Simvastatin improves sepsis-induced mortality and acute kidney injury via renal vascular effects. Kidney Int 69(9):1535-42.
Spitzer, A. L., and H. W. Harris. 2006. Statins attenuate sepsis. Surgery 139(3):283-7.
Kruger, P., K. Fitzsimmons, D. Cook, M. Jones, and G. Nimmo. 2006. Statin therapy is associated with fewer deaths in patients with bacteraemia. Intensive Care Med 32(1):75-9.
Kruger, S., and M. W. Merx. 2007. Nonuse of statins—a new risk factor for infectious death in cardiovascular patients? Crit Care Med 35(2):631-2.
Terblanche, M., Y. Almog, R. S. Rosenson, T. S. Smith, and D. G. Hackam. 2007. Statins and sepsis: multiple modifications at multiple levels. Lancet Infect Dis 7(5):358-68.
Dobesh, P. P., D. G. Klepser, T. R. McGuire, C. W. Morgan, and K. M. Olsen. 2009. Reduction in mortality associated with statin therapy in patients with severe sepsis. Pharmacotherapy 29(6):621-30.
Donnino, M. W., M. N. Cocchi, M. Howell, P. Clardy, D. Talmor, L. Cataldo, M. Chase, A. Al-Marshad, L. Ngo, and N. I. Shapiro. 2009. Statin therapy is associated with decreased mortality in patients with infection. Acad Emerg Med 16 (3):230-4.
Horn, M. P., S. M. Knecht, F. L. Rushing, J. Birdsong, C. P. Siddall, C. M. Johnson, T. N. Abraham, A. Brown, C. B. Volk, K. Gammon, D. L. Bishop, J. L. McKillip, and S. A. McDowell. 2008. Simvastatin inhibits *Staphylococcus aureus* host cell invasion through modulation of isoprenoid intermediates. J Pharmacol Exp Ther 326(1):135-43.
Chow, O. A., M. von Kockritz-Blickwede, A. T. Bright, M. E. Hensler, A. S. Zinkernagel, A. L. Cogen, R. L. Gallo, M. Monestier, Y. Wang, C. K. Glass, and V. Nizet. 2010. Statins enhance formation of phagocyte extracellular traps. Cell Host Microbe 8(5):445-54.
McDowell, S. A., Y. Ma, R. Kusano, and H. T. Akinbi. 2011. Simvastatin is protective during *Staphylococcus aureus* pneumonia. Current Pharmaceutical Biotechnology 12:1455-62.
Mahboobi, S. K., E. Z. Shohat, S. P. Jellinek, and M. Rose. 2006. Systemic infections can decrease the threshold of statin-induced muscle injury. South Med J 99(4):403-4.
Vincent, A., and J. A. Miller. 2006. Statins for sepsis: a cautionary note. Intensive Care Med 32(5):795.
Drage, S. M., V. S. Barber, and J. D. Young. 2007. Statins and sepsis: panacea or Pandora's box? Lancet Infect Dis 7 (2):80; author reply 80-1.
Golomb, B. A., and M. A. Evans. 2008. Statin adverse effects : a review of the literature and evidence for a mitochondrial mechanism. Am J Cardiovasc Drugs 8(6):373-418.
Brealey, D. A., M. Singer, and M. Terblanche. 2011. Potential metabolic consequences of statins in sepsis. Crit Care Med 39(6):1514-20.
Fessler, M. B. 2009. Simvastatin as a potential therapeutic for acute respiratory distress syndrome. Am J Respir Crit Care Med 180(10):1031; author reply 1031-2.
Surviladze, Z., A. Waller, J. J. Strouse, C. Bologa, O. Ursu, V. Salas, J. F. Parkinson, G. K. Phillips, E. Romero, A. Wandinger-Ness, L. A. Sklar, C. Schroeder, D. Simpson, J. Noth, J. Wang, J. Golden, and J. Aube. 2010. A Potent and Selective Inhibitor of CDC42 GTPase.
Endo, A. 1992. The discovery and development of HMG-CoA reductase inhibitors. J Lipid Res 33(11):1569-82.
Stankiewicz, T. E., K. L. Haaning, J. M. Owens, A. S. Jordan, K. Gammon, H. A. Bruns, and S. A. McDowell. 2010. GTPase activating protein function of p85 facilitates uptake and recycling of the beta1 integrin. Biochem Biophys Res Commun 391(1):443-8.
Sinensky, M. 2000. Recent advances in the study of prenylated proteins. Biochim Biophys Acta 1484(2-3):93-106.
Edwards, A. M. and R. C. Massey. 2011. How does *Staphylococcus aureus* escape the bloodstream? Trends in Microbiology 19(4):184-90.
Agarwal, V., and S. Hammerschmidt. 2009. CDC42 and the phosphatidylinositol 3-kinase-Akt pathway are essential for PspC-mediated internalization of pneumococci by respiratory epithelial cells. J Biol Chem 284(29):19427-36.
Van den Broeke, C., M. Radu, J. Chernoff, and H. W. Favoreel. 2010. An emerging role for p21-activated kinases (Paks) in viral infections. Trends Cell Biol 20(3):160-9.
Sinha, B., M. Herrmann, and K. H. Krause. 2000. Is *Staphylococcus aureus* an intracellular pathogen? Trends Microbiol 8(8):343-4.
Garzoni, C., and W. L. Kelley. 2009. *Staphylococcus aureus*: new evidence for intracellular persistence. Trends Microbiol 17(2):59-65.
Proctor, R. A., J. M. Balwit, and O. Vesga. 1994. Variant subpopulations of *Staphylococcus aureus* as cause of persistent and recurrent infections. Infect Agents Dis 3(6):302-12.
Menzies, B. E., and I. Kourteva. 1998. Internalization of *Staphylococcus aureus* by endothelial cells induces apoptosis. Infect Immun 66(12):5994-8.
Lowy, F. D. 2000. Is *Staphylococcus aureus* an intracellular pathogen? Trends Microbiol 8(8):341-3.
Sinha, B., and M. Herrmann. 2005. Mechanism and consequences of invasion of endothelial cells by *Staphylococcus aureus*. Thromb Haemost 94(2):266-77.
Foster, T. J. 2005. Immune evasion by staphylococci. Nat Rev Microbiol 3(12):948-58.
Que, Y. A., J. A. Haefliger, L. Piroth, P. Francois, E. Widmer, J. M. Entenza, B. Sinha, M. Herrmann, P. Francioli, P. Vaudaux, and P. Moreillon. 2005. Fibrinogen and fibronectin binding cooperate for valve infection and invasion in *Staphylococcus aureus* experimental endocarditis. J Exp Med 201(10):1627-35.
Hauck, C. R., and K. Ohlsen. 2006. Sticky connections: extracellular matrix protein recognition and integrin-mediated cellular invasion by *Staphylococcus aureus*. Curr Opin Microbiol 9(1):5-11.
Sendi, P., and R. A. Proctor. 2009. *Staphylococcus aureus* as an intracellular pathogen: the role of small colony variants. Trends in Microbiology 17(2):54-8.
Bokoch, G. M. 2005. Regulation of innate immunity by Rho GTPases. Trends Cell Biol 15(3):163-71.
Costerton, J. W., P. S. Stewart, and E. P. Greenberg. 1999. Bacterial biofilms: a common cause of persistent infections. Science 284(5418):1318-22.
Otto, M. 2008. Staphylococcal biofilms. Current Topics in Microbiology and Immunology 322:207-28.
Brady, R. A., J. G. Leid, J. H. Calhoun, J. W. Costerton, and M. E. Shirtliff. 2008. Osteomyelitis and the role of biofilms in in chronic infection. FEMS Immunology and Medical Microbiology 52(1):13-22.
Feid-Allah, H. M. 1981. Trisubstituted pyrazoles of possible antidiabetic and antibacterial activity Pharmazie 36:754-6.
Johnson, D. I. 1999. CDC42: An essential Rho-type GTPase controlling eukaryotic cell polarity. Microbiol Mol Biol Rev 63(1):54-105.
Tuchscherr, L., E. Medina, M. Hussain, W. Volker, V. Heitmann, S. Niemann, D. Holzinger, J. Roth, R. A. Proctor, K. Becker, G. Peters, and B. Loffler. 2011. *Staphylococcus aureus* phenotype switching: an effective bacterial strategy to escape host immune response and establish a chronic infection. EMBO Mol Med 3(3):129-41.
Chorianopoulos, E., F. Bea, H. A. Katus, and N. Frey. 2009. The role of endothelial cell biology in endocarditis. Cell & Tissue Research 335(1):153-63.
Zheng, Y., S. Bagrodia, and R. A. Cerione. 1994. Activation of phosphoinositide 3-kinase activity by CDC42Hs binding to p85. J Biol Chem 269(29):18727-30.
Friesen, J. A., and V. W. Rodwell. 2004. The 3-hydroxy-3-methylglutaryl coenzyme-A (HMG-CoA) reductases. Genome Biol 5(11):248.

* cited by examiner

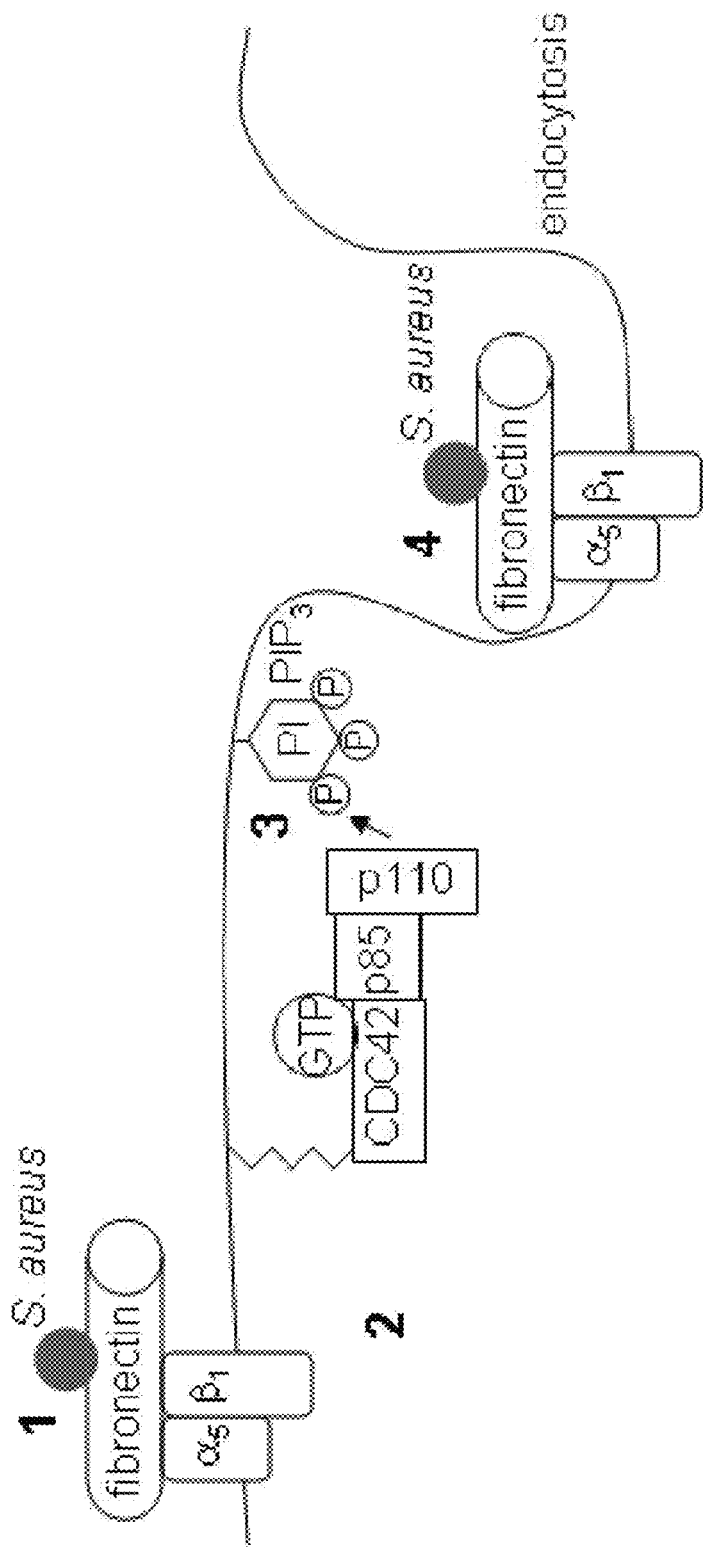

Figure 4A1
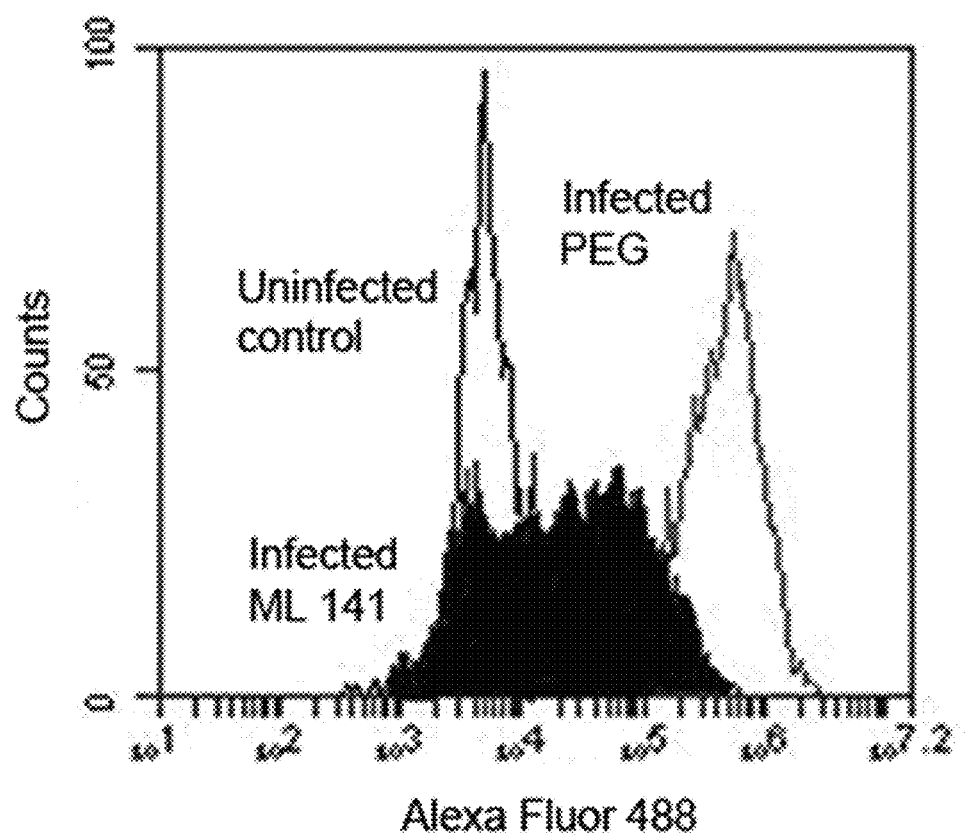

Figure 4A2
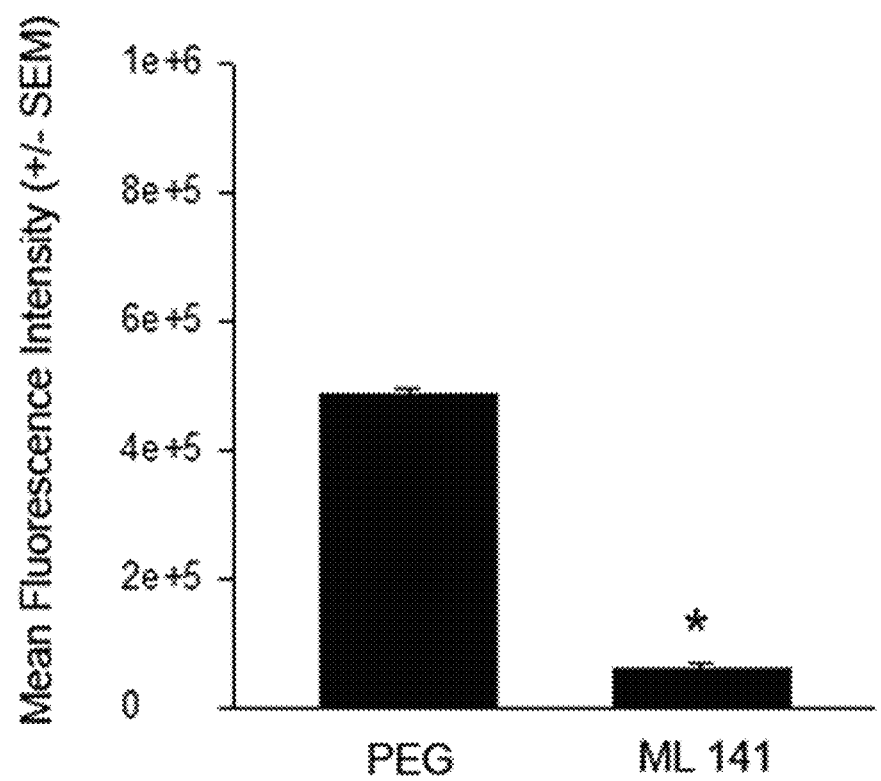

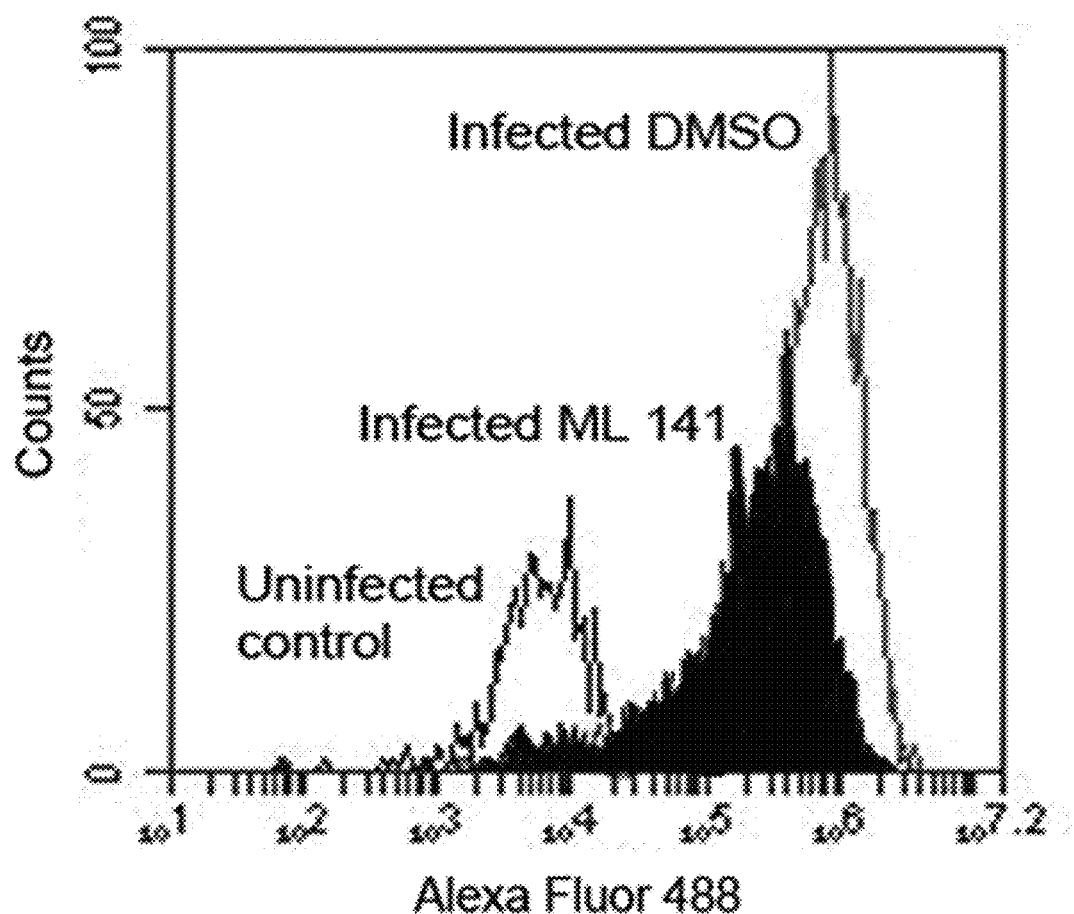
Figure 4B1

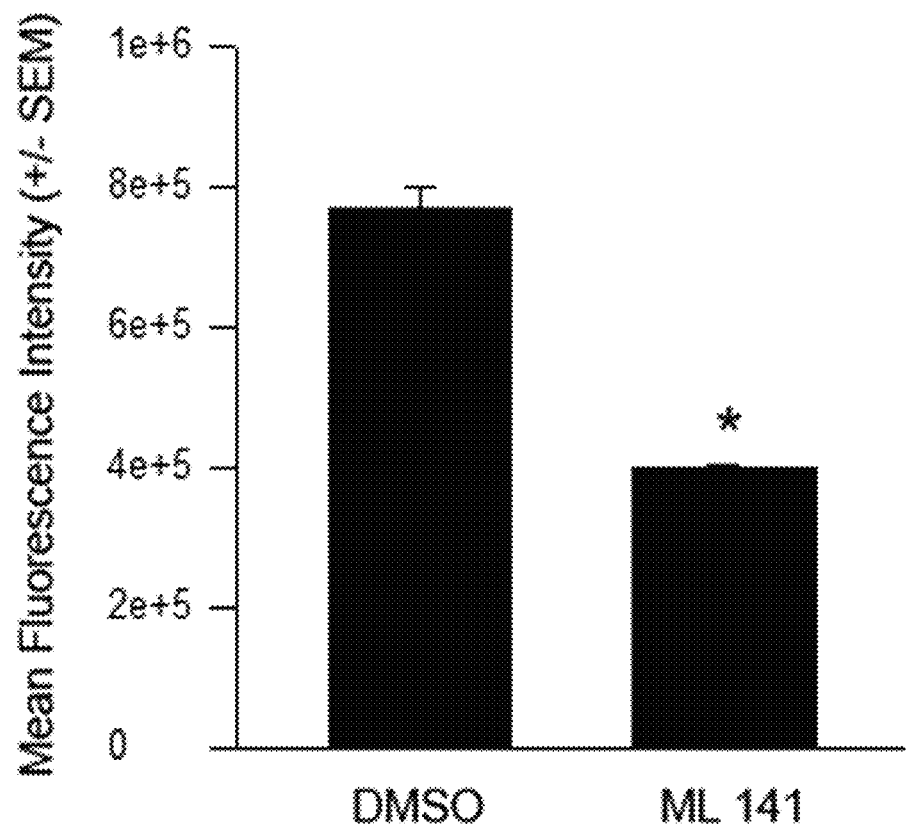
Figure 4B2

_US 9,259,415 B2_

EFFICACY IN TREATING BACTERIAL INFECTIONS

REFERENCE TO RELATED APPLICATIONS

The present application claims priority from U.S. Provisional Patent Application Ser. No. 61/601,807, filed on Feb. 22, 2012, the disclosure of which is expressly incorporated by reference. The present application also claims priority from U.S. Provisional Patent Application Ser. No. 61/644,798, filed on May 9, 2012, the disclosure of which is expressly incorporated by reference. The present application also claims priority from U.S. Provisional Patent Application Ser. No. 61/671,054, filed on Jul. 12, 2012, the disclosure of which is expressly incorporated by reference.

GOVERNMENT LICENSE RIGHTS

This invention was made with government support under Grant No. 1 R15 HL092504-01 awarded by the National Institutes of Health, National Heart Lung and Blood Institute and Grant No. U54 MH084690 awarded by the National Institutes of Health. The U.S. Government has certain rights in the invention disclosed herein.

FIELD

The present disclosure relates to molecules that function as selective modulators (i.e., inhibitors and agonists) of the Ras-homologous (Rho) family of small GTPases and, in particular, CDC42 GTPase, and their use to treat bacterial infection including systemic infection from sources such as *Staphylococcus aureus*.

BACKGROUND

In the US, *S. aureus* is the most common etiologic agent in systemic infection and in biofilm-mediated infection of implanted devices. Treatment is complicated by the steady emergence of antibiotic resistance and by increases in elderly, immunocompromised populations, prevalence in the use of surgically implanted devices, and by the ability of both resistant and susceptible strains to persist asymptomatically months to years after the withdrawal of antimicrobial therapy. Severe infection is associated with high rates of mortality (11-43%) and with chronic, debilitating morbidities that include infective endocarditis, osteomyelitis, and recurrent lung infection. The current cost-of-care is estimated at $10 billion annually for treatment of infection by methicillin resistant *S. aureus* (MRSA) alone.

Strategies for improving treatment options have included the creation of new antibiotics and the development of adjunctive therapeutics.

SUMMARY

We have examined compounds that inhibit host cell invasion yet through a mevalonate independent mechanism. It was found that ML 141 inhibits endothelial cell invasion and intracellular persistence (see FIGS. 1, 2A and 2B). The mode-of-action of ML 141 is distinct from that of other therapeutics used in treating invasions, such as some statins. ML 141 inhibits GTP-binding at the activation site of CDC42. Some statins compete for substrate binding within the catalytic site of 3-hydroxy-3-methylglutary (HMG)-CoA reductase. Similar to ML 141, some statins functionally inactivate CDC42 through an indirect mechanism. ML 141 binds directly to CDC42 with a high degree of specificity for this small-GTPase. Inhibition by some statins is not specific for CDC42, but rather is due to diminished levels of isoprenoid intermediates formed from mevalonate within the cholesterol biosynthesis pathway. The isoprenoid intermediates farnesyl pyrophosphate and geranylgeranyl pyrophosphate provide membrane anchoring and protein-protein interactions for CaaX-motif containing proteins that include CDC42. In this way, ML 141 and some statins functionally inhibit CDC42 yet through different mechanisms.

Host CDC42 may provide a central target in the treatment of invasive infection. CDC42 is used by *S. aureus* to facilitate uptake into host cells and is targeted by staphylococcal toxins for tunneling through endothelial cells to the underlying matrix. This selective use of CDC42 is consistent with invasion by *Streptococcus pneumonia*, the etiologic agent of community-acquired pneumonia, in that redundancy amongst small-GTPases fails to restore invasiveness in cells expressing dominant-negative CDC42. The use of CDC42 to gain host cell entry extends beyond bacterial pathogens to viral infection, facilitating both uptake and replication.

Until recently, the biological relevance of invasiveness by *S. aureus* had been challenged. *S. aureus* had been considered an extracellular pathogen, and intracellular residency appeared to be an in vitro artifact. However, in vivo and clinical evidence supports the concept that intracellular residency by *S. aureus* contributes significantly to pathogenesis by stimulating pro-inflammatory and pro-coagulant responses, by enabling evasion of antibiotics and immune cells, and by establishing intracellular bacterial reservoirs as sources of chronic infection. Numerous questions exist regarding the biological consequence of host cell invasion by *S. aureus*, including whether uptake by non-immune cells serves solely as a mechanism of evasion, or whether this uptake serves as a mechanism of host defense. Studies using ML 141 investigate whether the direct inhibition of CDC42 impedes the roles of this protein in innate immunity.

ML 141 remains largely uncharacterized with respect to antibacterial activity. Synthesis initially was described by Faid-Allah et al. within a series of compounds predicted to possess antibacterial activity. However, antimicrobial data were not presented. Surviladze et al. found that the compound inhibits GTP-loading of CDC42 with a high degree of specificity for this small-GTPase.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 2A is a schematic model of *Staphylococcus aureus* host cell invasion in the absence of ML 141. Step 1: In the absence of ML 141, *S. aureus* bound to host fibronectin interacts with the host cell integrin $\alpha_5\beta_1$, stimulating GTP-loading and activation of CDC42. Step 2: GTP-loading of CDC42 increases affinity for the p85α regulatory subunit of phosphoinositide 3-kinase (PI3K). CDC42, coupled to PI3K through the p85α subunit, positions the catalytic domain p110α in proximity with phosphoinositide 4,5-bisphosphate (PI$_{4,5}$). Step 3: The product of the phosphorylation of PI$_{4,5}$ by p110α is PI 3,4,5-trisphosphate (PIP$_3$), capable of promoting endocytosis of the bacterium/fibronectin/integrin complex, as illustrated by Step 4.

FIG. 4A1 illustrates by histogram overlay how ML 141 inhibits host cell invasion. Human umbilical vein endothelial cells (HUVEC) were pretreated (18 hours) with the vehicle control polyethylene glycol (PEG) or ML 141 (10 µM) suspended in PEG. Following infection by Alexa Fluor 488-labeled Staphylococcus aureus (1 hour), extracellular bacteria were removed using the antimicrobials gentamicin and lysostaphin. Infected cells (identified by 488 fluorescence) were detected by flow cytometry and represented by histogram overlay.

FIG. 4A2 illustrates by averaged mean fluorescence intensity values how ML 141 inhibits host cell invasion. Human umbilical vein endothelial cells (HUVEC) were pretreated (18 hours) with the vehicle control polyethylene glycol (PEG) or ML 141 (10 µM) suspended in PEG. Following infection by Alexa Fluor 488-labeled Staphylococcus aureus (1 hour), extracellular bacteria were removed using the antimicrobials gentamicin and lysostaphin. Infected cells (identified by 488 fluorescence) were detected by flow cytometry and represented by histogram overlay as illustrated in FIG. 4A1 and averaged mean fluorescence intensity values (*less than vehicle control; $p \leq 0.001$ by Student's t-test; n=3-5/treatment).

FIG. 4B1 illustrates by histogram overlay how ML 141 inhibits host cell invasion. Human umbilical vein endothelial cells (HUVEC) were pretreated (18 hours) with the vehicle control dimethyl sulfoxide (DMSO) or ML 141 (10 µM) suspended in dimethyl sulfoxide (DMSO). Following infection by Alexa Fluor 488-labeled Staphylococcus aureus (1 hour), extracellular bacteria were removed using the antimicrobials gentamicin and lysostaphin. Infected cells (identified by 488 fluorescence) were detected by flow cytometry and represented by histogram overlay.

FIG. 4B2 illustrates by averaged mean fluorescence intensity values how ML 141 inhibits host cell invasion. Human umbilical vein endothelial cells (HUVEC) were pretreated (18 hours) with the vehicle control dimethyl sulfoxide (DMSO) or ML 141 (10 µM) suspended in dimethyl sulfoxide (DMSO). Following infection by Alexa Fluor 488-labeled Staphylococcus aureus (1 hour), extracellular bacteria were removed using the antimicrobials gentamicin and lysostaphin. Infected cells (identified by 488 fluorescence) were detected by flow cytometry and represented by histogram overlay as illustrated in FIG. 4B1 and averaged mean fluorescence intensity values (less than vehicle control; $p \leq 0.001$ by Student's t-test; n=3-5/treatment).

Figure 1:
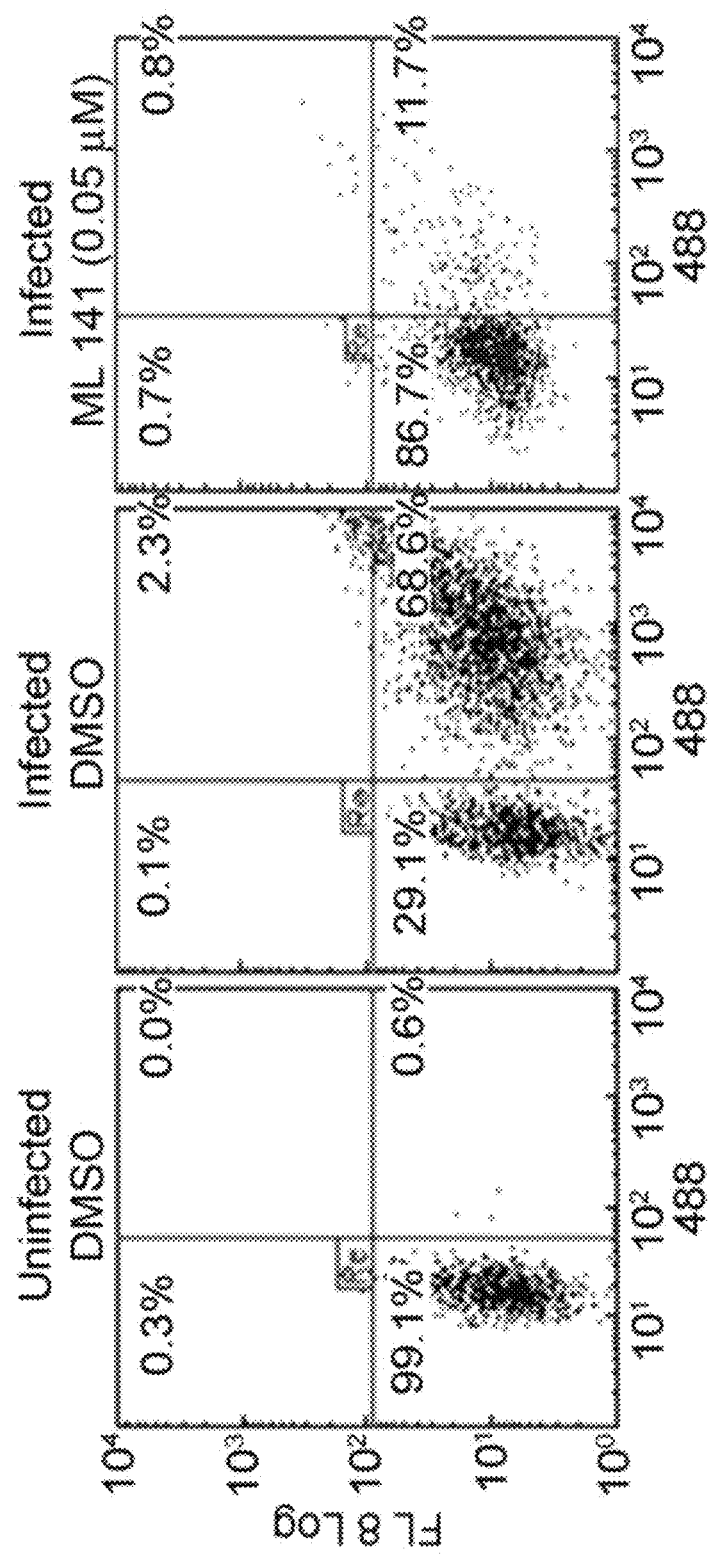
FIG. 1 illustrates ML 141 limits host cell invasion. The monocytic cell line U937 was pretreated with the vehicle control dimethyl sulfoxide (DMSO) or with ML 141 (0.05 μM) followed by infection with Alexa Fluor 488-labeled *S. aureus* (1 hour). The % of 488+ cells decreased with ML 141 treatment.

18-20 h prior to infection with *Staphylococcus aureus* (1 h). Actin was detected using Alexa Fluor 488 phalloidin. 200 cells/treatment were evaluated from randomly selected fields. Data are presented as the % of cells in which actin stress fibers were not detected. Scale bar is 50 μm.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

Innovation

The ML 141 compound has been used to address whether targeting CDC42 limits persisting intracellular populations, diminishing this source of chronic infection and initiates pleiotropic effects by interrupting the PI3K signaling pathway.

Findings will impact the characterization of this potentially first-in-class molecule for the development of adjunctive therapeutics. Moreover, data from the in vivo toxicity study as well as the synthesis of analogs potentially will be of use to the broader scientific community for exploring the role of CDC42 in a range of disease states.

Approach

Preliminary Data

Direct Inhibition of CDC42 Diminishes Host Cell Invasion:

Specific pharmacologic inhibition of CDC42 has been examined to determine whether it is sufficient in the inhibition of host cell invasion by *S. aureus*. It was found that pretreatment (0.05 □M, 1 hour) decreased invasion by *S. aureus* as shown in FIG. 1. Host cell cytotoxicity was undetectable below 30 □M in vitro. The highest concentration of ML 141 introduced in vivo without detectable toxicity was 100 mg/kg body weight [BW]. The compound was dissolved in polyethylene glycol and administered as a single intraperitoneal injection to C57BL/6 mice.

Figure 3:
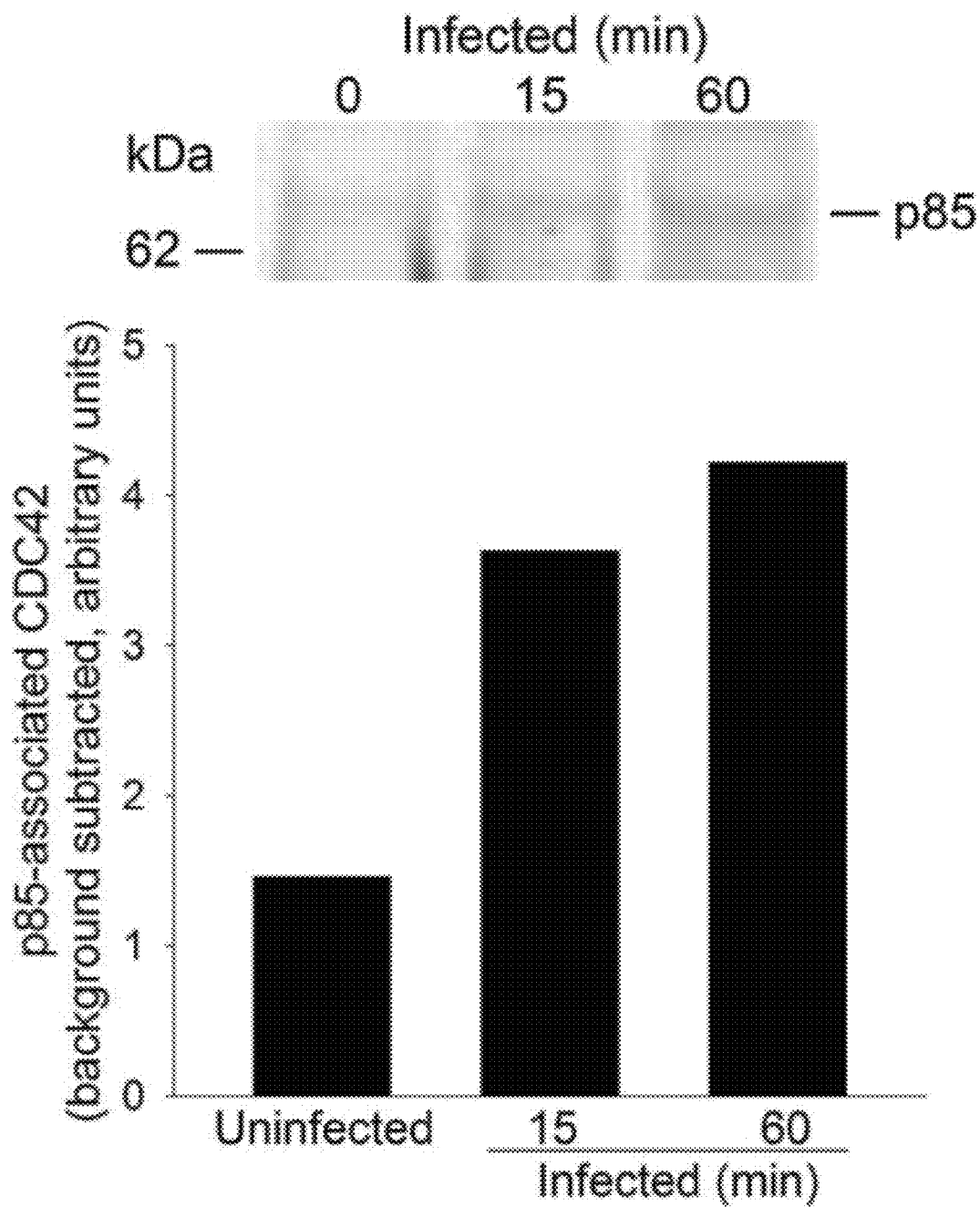
FIG. 3 illustrates how invasion stimulates coupling between CDC42 and the downstream effector phosphoinositide 3-kinase (PI3K) p85. Host cells (human embryonic kidney cells) were infected for 15 or 60 min, lysates immunoprecipitated (IP) with anti-CDC42, and immunoblot (IB) probed with anti-p85 followed by Alexa Fluor anti-rabbit 800CW. Fluorescence was detected using the Odyssey Infrared Imaging System. Integrated intensities and background correction were performed using Odyssey software.

ML 141 Diminishes Intracellular Persistence:

Host Invasion Stimulates Coupling Between CDC42 and PI3Kp85□:

Affinity between the downstream regulator PI3 Kp85□ and CDC42 is enhanced by GTP-loading of CDC42. Earlier research has demonstrated that *S. aureus* host cell invasion stimulates GTP-loading of CDC42, raising the possibility that invasion potentially results in increased coupling between these proteins. Within 15 min of host cell invasion, it was found that p85□-associated CDC42 had increased (see FIG. 3).

Summary of Preliminary Data

Preliminary research indicates that ML 141 inhibits invasiveness and intracellular persistence potentially through impaired PI3K signaling. The following Experimental Sections examine ML 141 to investigate the targeting of CDC42 in ameliorating clinically relevant, persistent infection by *S. aureus*.

Figure 2B:
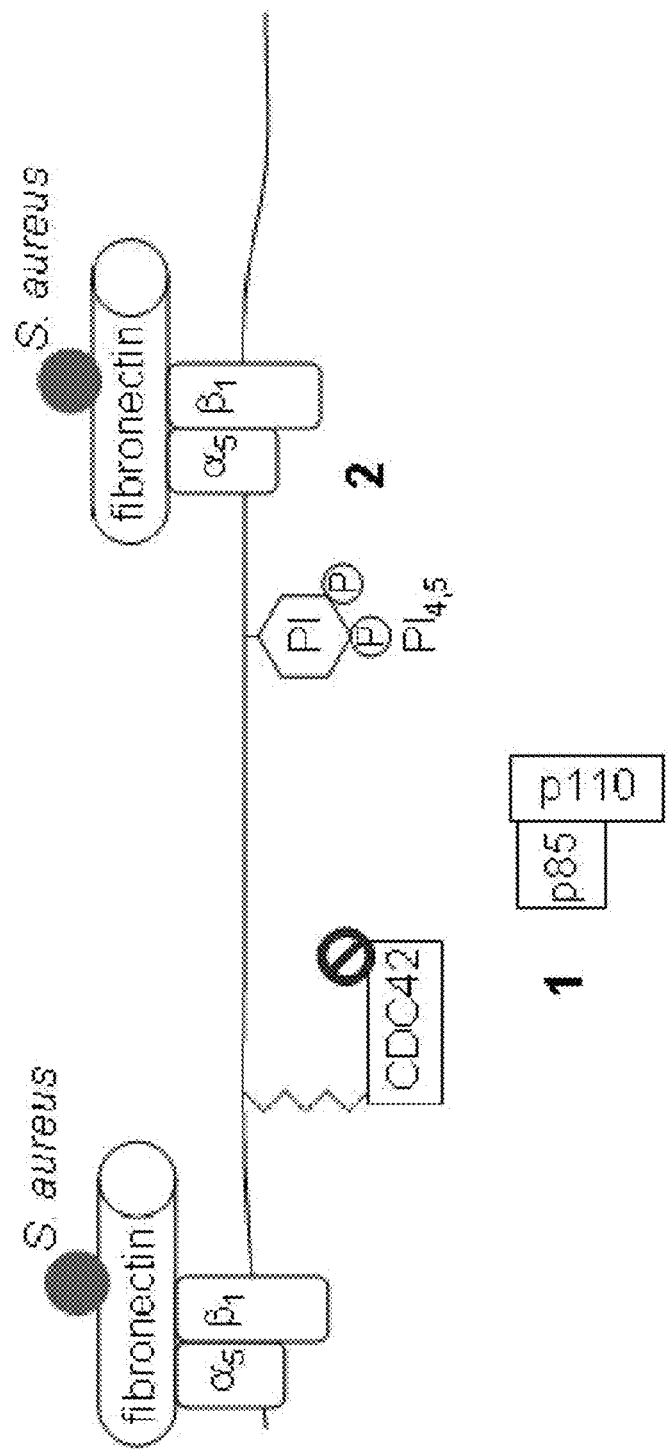
FIG. 2B is a schematic model of Staphylococcus aureus host cell inhibition by ML 141. Step 1: In response to the inhibition of GTP-loading of CDC42 by ML 141, CDC42 remains uncoupled from p85α. Consequently, p110α remains within the cytosol. By sequestering p110α within the cytosol, membrane-bound PI$_{4,5}$ is not accessible, diminishing PIP$_3$ production. Step 2: In the absence of PIP$_3$, endocytic uptake of the bacterium/fibronectin/integrin complex is limited, protecting the host cell from bacterial invasion (models are based on references indicated in text and on current study).

Experimental Section 1: Examine ML 141 in Limiting Persisting *S. Aureus* Infection Rationale Increasing evidence supports the hypothesis that *S. aureus* infection persists through pathogenic mechanisms that includes survival within host cells. The focus of Section 1 is on exploring new strategies for limiting infection by this mechanism. It was found that ML 141 decreased initial host cell invasion and the number of persistently infecting, intracellular bacteria (see FIGS. 1 and 2). A subset of bacteria that persist intracellularly can convert phenotypically to what have been termed "small colony variants" (SCV). This phenotypically distinct population has been the source of controversy, questioned as a laboratory artifact. However, recent in vivo and clinical evidence supports the existence of this population and its potential contribution to chronic, recurrent infection. These variants, upon release from persistently infected host cells, invade new host cells more aggressively than their parental strain. It is believed that ML 141 limits this potential source of recurrent infection by inhibiting their uptake into new host cells, increasing their clearance by antibiotic therapy and exposure to surveillance by immune cells. Alternatively, ML 141 would impair uptake of *S. aureus* by non-immune cells as a mechanism of clearance.

Study 2

Materials and Methods

Reagents for Cultured Cells:

The following were used at the concentrations and durations indicated within each figure or method described below: paraformaldehyde (Electron Microscopy Sciences, Hatfield, Pa.); dimethyl sulfoxide (DMSO) and bovine serum albumin (BSA, Thermo Fisher Scientific, Pittsburgh, Pa.); tryptic soy agar (TSA) and broth (TSB), saponin, lysostaphin, gentamicin, triton, polyethylene glycol (PEG), and formaldehyde (Sigma-Aldrich, St. Louis, Mo.); phosphate buffered saline (PBS), Attachment Factor, M200, Low Serum Growth Supplement (LSGS), rabbit anti-mouse IgG, Alexa Fluor 488 phalloidin, and L-glutamine (Life Technologies, Carlsbad, Calif.); XTT (Biotium, Hayward, Calif.); and fetal bovine serum (FBS, Atlanta Biologicals, Lawrenceville, Ga.). 4-[3-(4-methoxyphenyl)-5-phenyl-3,4-dihydropyrazol-2-yl]benzenesulfonamide (ML 141) was generously provided by Dr. Jennifer Golden of the University of Kansas Specialized Chemistry Center or was prepared following standard synthetic procedures.

Cell Culture and Compound Treatment:

In one embodiment, human umbilical vein endothelial cells (HUVEC, Life Technologies) are cultured in M200 medium supplemented with LSGS. RAW 264.7 cells (American Type Culture Collection, ATCC, Manassas, Va.) are cultured in RPMI supplemented with 10% FBS and L-glutamine. All cell types are maintained at 5% $CO_2$, 37° C., in 75 $cm^2$ vented cap flasks (Thermo-Fisher). For assays, cultured cells are plated at $1 \times 10^5$ cells/ml in 35 mm culture dishes coated with Attachment Factor. The next day, cells are pretreated in culture medium containing the vehicle control or ML 141. For compound delivery, ML 141 first is suspended into DMSO or into PEG at a concentration of 5 mM. The 5 mM solution is diluted to 1 mM in the solvent and then diluted to the final concentration for each experiment in either serum-containing or serum-free medium. For vehicle control treatment, the same volume of PEG or DMSO as that of ML 141 is added to medium. The following day, the invasion assay is performed. For the shorter duration experiments, compound is added on the same day as the invasion assay, 1 hour prior to bacteria. Because in vitro data indicate that ML 141 is a reversible inhibitor, bacteria is added directly to medium containing vehicle control or ML 141.

In another embodiment, HUVEC (Millipore, Billerica, Mass.) are cultured in EndoGRO LS Complete Media (Millipore) and are maintained at 5% $CO_2$, 37° C., in 75 $cm^2$ vented cap flasks (Thermo-Fisher). For the invasion assay, cultured cells are plated at $1 \times 10^4$ cells/ml in 96-well culture dishes coated with Attachment Factor. The next day, cells are pretreated in culture medium containing the vehicle control, ML 141, or ML 141 structural analog. For compound delivery, ML 141 and structural analogs first are suspended into PEG at a concentration of 5 mM. The 5 mM solution is diluted to 1 mM in the solvent and then is diluted to the final concentration for each experiment in serum containing medium. For vehicle control treatment, the same volume of PEG as that of ML 141 or of ML 141 structural analog is added to the medium. The following day, the invasion assay is performed. Bacteria are added directly to medium containing vehicle control, ML 141, or the ML 141 structural analog.

Invasion Assay:

Two days prior to the assay, TSB is inoculated with *S. aureus* (American Type Culture Collection #29213) and incubated overnight (225 rpm, 37° C.). Bacteria are subcultured the next day into fresh TSB. On the day of the assay, bacteria are pelleted (10000×g, 37° C., 3 min), are washed in saline, are pelleted as above, are resuspended in saline, then fluorescently are labeled by incubation with rabbit anti-mouse IgG Alexa Fluor 488 (final concentration 8 µg/ml, RT, 20 min). Protein A, a *S. aureus* cell surface protein, avidly binds IgG thereby labeling the bacteria. Labeled bacteria are washed twice as above and are resuspended to $3 \times 10^8$ CFU/ml in saline. Host cells are incubated with the bacteria for 1 hour ($1.2 \times 10^8$ CFU/ml for same-day recovery, $5 \times 10^6$ for recovery after 48 hours, $1.4 \times 10^7$ CFU/ml; 5% $CO_2$, 37° C.). Following infection, extracellular bacteria are removed by extensive washes with PBS and incubation of the host cells with antimicrobials that have limited mammalian membrane permeability (lysostaphin, 20 µg/ml and gentamicin, 50 µg/ml; 45 min for same-day recovery studies, 48 hours for 2-day recovery studies; 5% $CO_2$, 37° C.). To detect the level of infection using flow cytometry, cells that have been infected with fluorescently-labeled bacteria are washed extensively with PBS, lifted from 96-well plate by incubation with trypsin, washed extensively in FACS buffer (2% BSA/0.1% sodium azide/PBS), fixed (FACS buffer containing 0.74% formaldehyde), and are counted using an Accuri flow cytometer (BD, Franklin Lakes, N.J.). They are also lifted from culture dishes using cell scrapers, pelleted, fixed (1% BSA/0.74% formaldehyde/PBS), and are counted using an Accuri flow cytometer. For enumeration of the infecting bacteria, intracellular bacteria are released from host cells using 1% saponin/PBS (20 min, 5% $CO_2$, 37° C.) and serial dilutions are plated on TSA (16 hours, 37° C.). For infection under serum free conditions, bacteria first are incubated in FBS (15 minutes, RT) followed by extensive washing. The serum incubation provided extracellular matrix proteins that facilitate invasive infection.

Cytotoxicity Assay:

HUVEC are plated at a density of $1.2 \times 10^4$ cells/ml into 96-well dishes coated with Attachment Factor. The next day, cells are pretreated with the vehicle control DMSO or with ML 141 (18 hours). An XTT-reducing assay is performed and absorbance read at 490 nanometer using a Bio-Rad plate reader.

Assessment of Bactericidal Activity:

HUVEC are pretreated with the vehicle control DMSO or with ML 141 (18 hours) then incubated with $5 \times 10^6$ CFU/ml (1 hour). Following infection, the medium from each plate is removed, is serially diluted into saline, and is plated on fresh blood agar plates. The next day, colony counts are performed and hemolysis is recorded.

Immunofluorescence:

HUVEC are plated at $1 \times 10^5$ cells/ml into 35 mm glass-bottom dishes (MatTek, Ashland, Mass.) are coated with Attachment Factor, are pretreated, and are infected ($1.2 \times 10^8$ CFU) as described above. Following infection, cells are washed with 1×PBS, fixed (4% paraformaldehyde/PBS, 30 min), permeabilized, blocked (0.1% Triton, 1% bovine serum albumin, 30 min), and incubated with Alexa Fluor 488 phalloidin (1:40). Confocal images are acquired using an inverted Zeiss Axiovert200 microscope equipped with a plan-apochromat 40×, 1.2 NA water immersion lens with correction collar and LSM 5 Pascal scan head. Alexa 488 is excited by the 488 nanommeter Ar laser line and is detected using a 505-530 nanometer bandpass filter. Z-sectioning and frame size are set to Nyquist sampling. Maximum pixel projections from the Z-stacks are generated and are analyzed for actin morphology.

Statistical Analyses:

Normally distributed data are analyzed by Student's t-test when the comparison was limited to 2 groups or by one-way ANOVA followed by Student-Newman-Keuls post-hoc analysis when 3 or more groups were compared (Sigma Stat, Systat, Point Richmond, Calif.). Differences between groups were considered statistically significant at p<0.05.

Results and Discussion

ML 141 Limits Host Cell Invasion.

Figure 5:
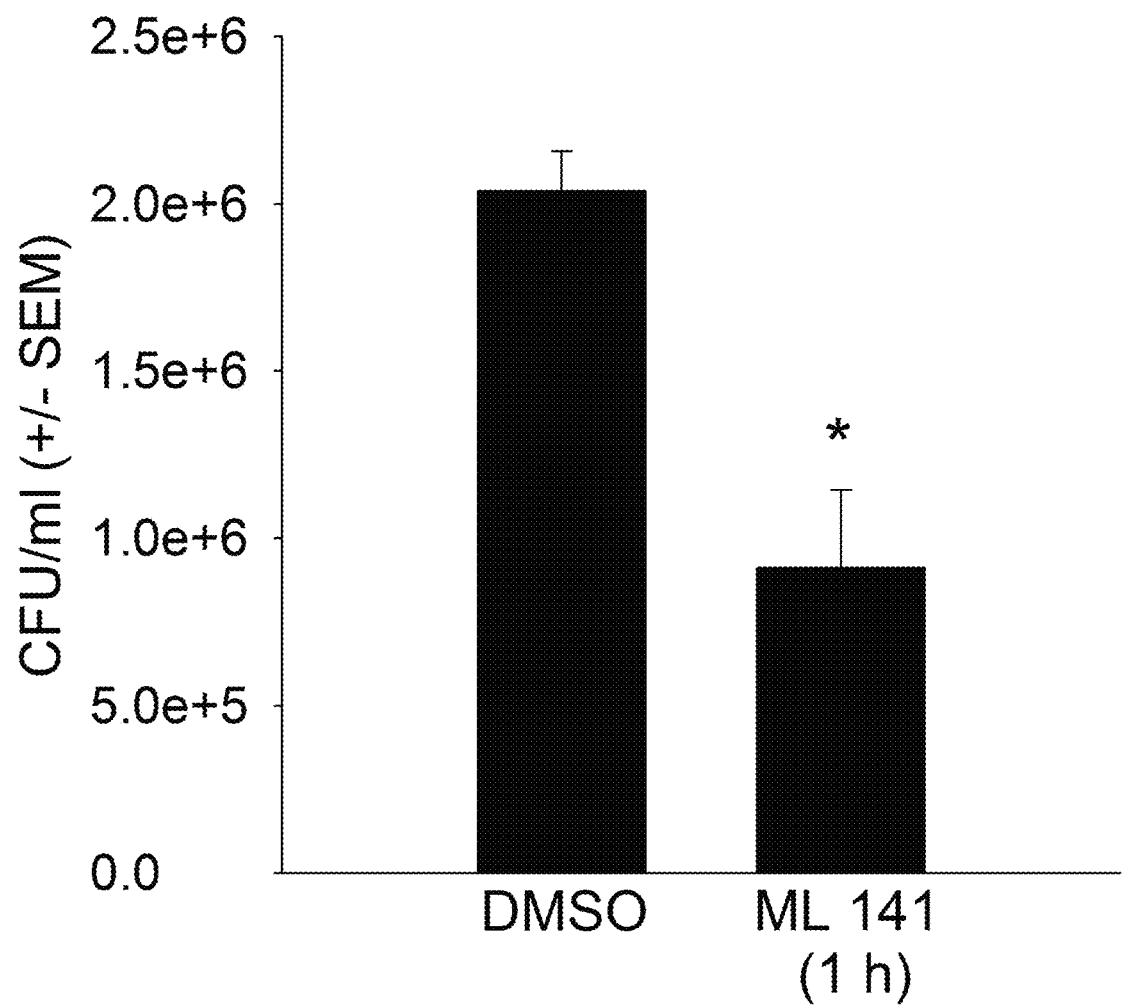
FIG. 5 is a graph illustrating ML 141 inhibiting invasion with shorter duration exposure under serum starved conditions. RAW 264.7 cells were serum-starved overnight then pretreated for 1 hour with the vehicle control dimethyl sulfoxide (DMSO) or with ML 141 (10 µM). Following infection with Staphylococcus aureus (1 hour), extracellular bacteria were eliminated using the antimicrobials gentamicin and lysostaphin (45 minutes), and intracellular bacteria recovered by permeabilizing the host cells. Serial dilutions of the recovered intracellular bacteria were incubated on tryptic soy agar, colonies enumerated, and colony forming units (CFU)/ml calculated (less than vehicle control; $p \leq 0.05$ by Student's t-test; n=3/treatment).

Earlier work had indicated that CDC42 activity is stimulated by *S. aureus* host cell invasion and that limiting CDC42 function using a genetic strategy led to a reduction in *S. aureus* invasiveness. To determine whether specific, pharmacologic inhibition of CDC42 is sufficient to inhibit invasion by *S. aureus*, HUVEC are pretreated (18 hours) with ML 141 (10.0 µM) or with the vehicle control PEG and are infected for 1 hour. ML 141 treatment decreased invasion by more than 80% (p≤0.001 by Student's t-test, FIG. 4, Panel A). When ML 141 is delivered in DMSO rather than in PEG, inhibition nears 50% (Panel B). Inhibition is detectable when treatment was reduced from 18 hours to 1 hour under serum-starved conditions (FIG. 5). ML 141 inhibited invasion in all cell types examined (HUVEC, HEK, U-87 MG, RAW and A549).

Figure 6A:
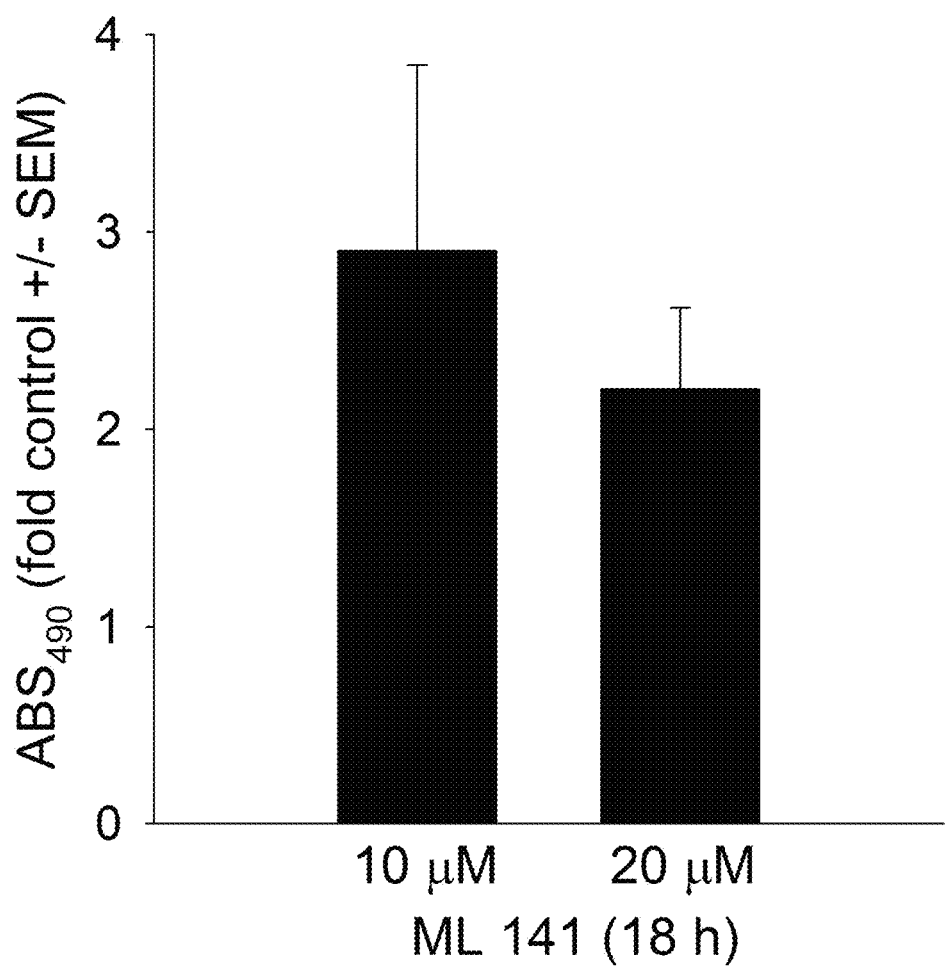
FIG. 6A illustrates that neither cytotoxicity nor bactericidal activity is detected. Human umbilical vein endothelial cells (HUVEC) were pretreated (18 hours) with the vehicle control polyethylene glycol (PEG) or with ML 141 and viability assessed using an XTT assay. The formazan dye produced in living cells was detectable at an absorbance wavelength of 490 nanometer and used as an indicator of cell viability. Absorbance values were not different amongst the groups ($p > 0.05$ by one-way ANOVA; n=3/treatment).
Figure 6B:
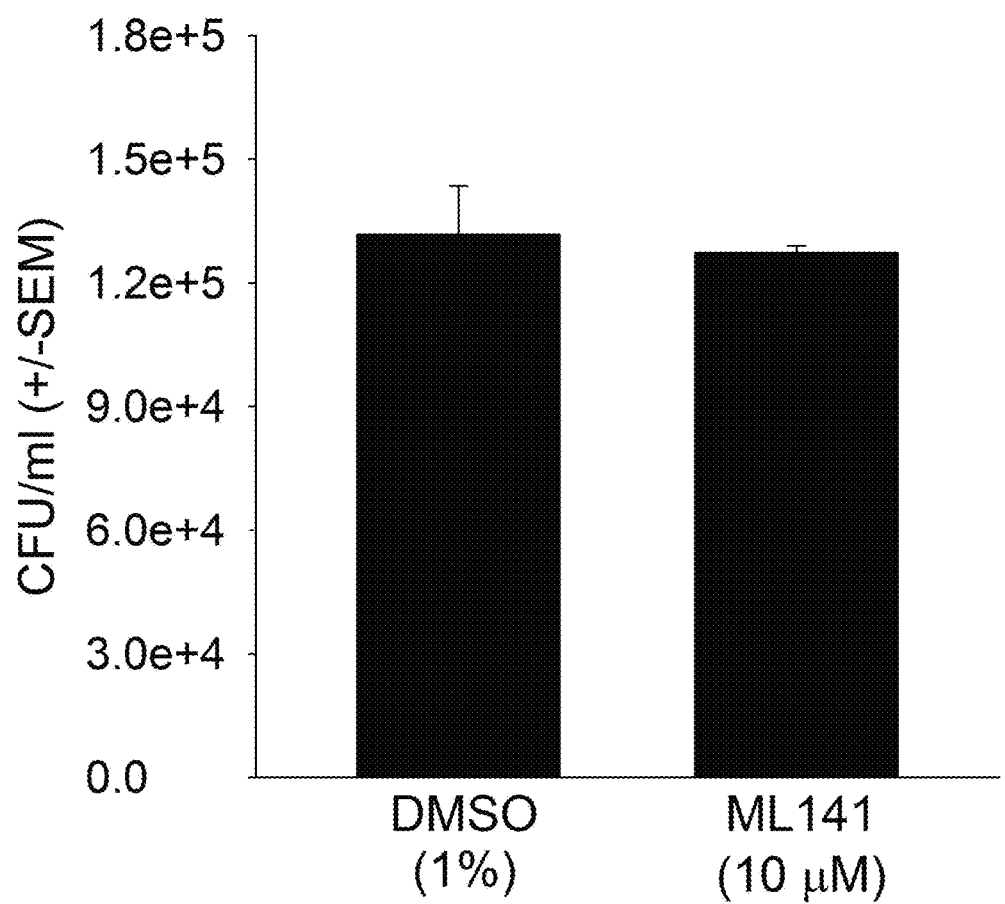
FIG. 6B illustrates that neither cytotoxicity nor bactericidal activity is detected. Cultures of Staphylococcus aureus that had been incubated with the vehicle control DMSO or with ML 141 (1 hour, 37° C., 225 rpm) were serially diluted, plated onto tryptic soy agar, and incubated (18 hours, 37° C.). Colonies were enumerated and colony forming units (CFU)/ml determined. CFU/ml were not different amongst the groups ($p > 0.05$ by Student's t-test; n=2/treatment).

The number of uninfected cells is greatest when ML 141 has been delivered in PEG rather than in DMSO (FIG. 4 Panels A and B), suggesting that PEG enhanced the delivery of ML 141. PEG is a well-characterized, hydrophilic polymer that can increase the delivery of hydrophobic compounds into mammalian cells. The increased effectiveness of ML 141 when delivered in PEG may be attributable to an increase in the solubility of ML 141. Evidence supporting this concept is that suspension in PEG enhances the solubility of celecoxib, a COX-2 inhibitor that is structurally similar to ML 141. That PEG generally is well-tolerated with minimal toxicity is supported by the finding that cytotoxicity was not observed at the concentrations used in the invasion assay (FIG. 6).

Cytotoxicity and Bactericidal Activity were not Detected.

To determine whether host or bacterial cell death contributed to the decreases in recovered bacteria, cytotoxicity and bactericidal activity are assessed. Cytotoxicity is not detectable in HUVEC treated overnight in ML 141 in the PEG solvent (FIG. 6, Panel A; p0.05 by one-way ANOVA). Bactericidal activity was not detected (Panel B). These findings suggest that the decreases in infected host cells and in recovered bacteria are attributable to diminished host cell invasion rather than to host cell death or to bactericidal activity of the compound.

Intracellular Populations Remain Suppressed Over Time.

Figure 7:
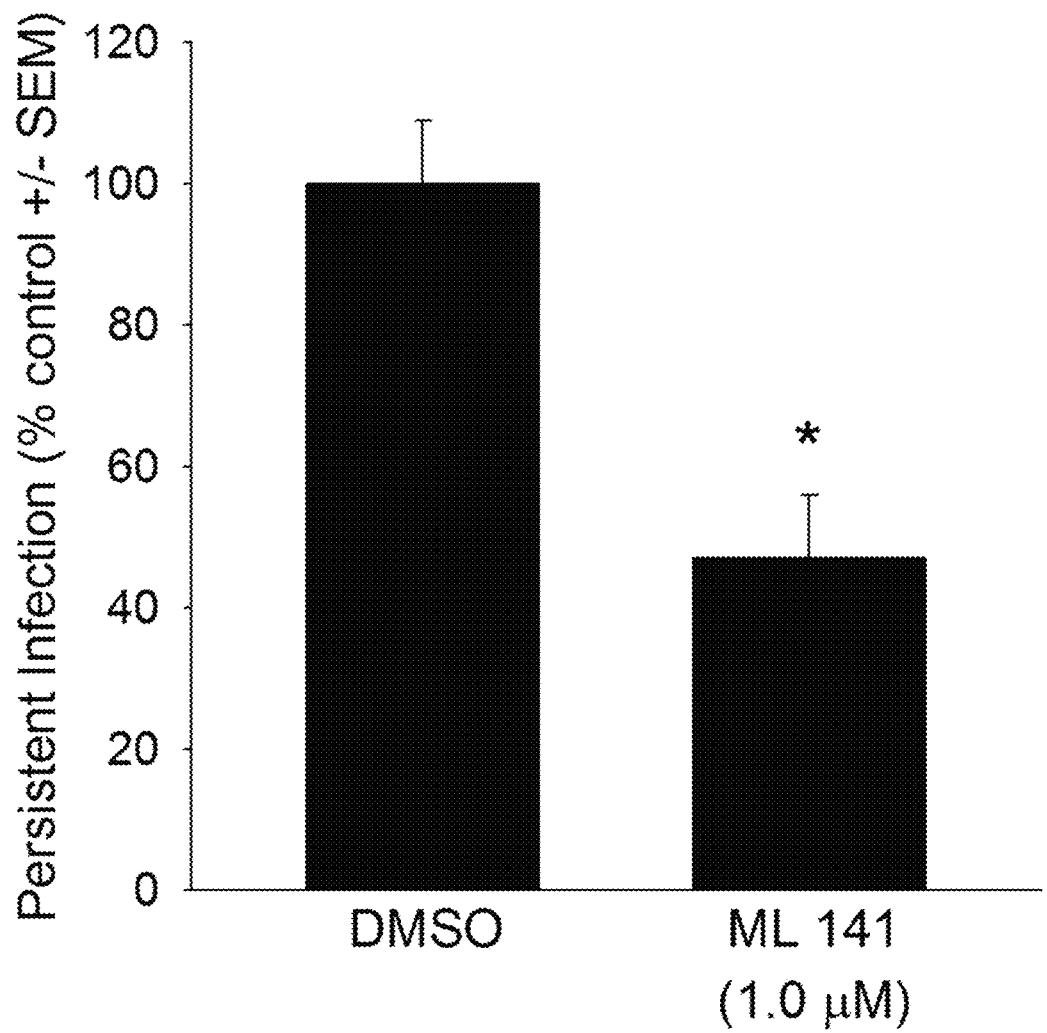
FIG. 7 is a graph illustrating suppression of intracellular population sustained over time. Human umbilical vein endothelial cells (HUVEC) were pretreated (1.0 µM, 18 hours) with the vehicle control dimethyl sulfoxide (DMSO) or ML 141 and infected with Staphylococcus aureus (1 hour). At 48 hours, intracellular bacteria were recovered, serial dilutions incubated on tryptic soy agar and colonies enumerated. Data are presented as % control, ±SEM (less than vehicle control; $p \geq 0.05$ by Student's t-test; n=3-5/treatment).

Intracellular bacterial populations can continue to proliferate, therefore, we next examine whether the intracellular bacterial population within ML 141-treated host cells returned to control levels over time. HUVEC are pretreated with vehicle control or with ML 141 (1.0 µM, 18 hours), infected for 1 hour, and bacterial levels within host cells are assessed at 48 hours post infection. These experiments are pursued in endothelial cells as a model system for growth of intracellular reservoirs and because of the central role played by the endothelial cell in the pathogenesis of endocarditis. Treatment with ML 141 diminished the number of viable bacteria recovered 48 hours post-infection (FIG. 7).

Intracellular persistence by *S. aureus* enables the pathogen to evade antibiotic therapies and surveillance by immune cells. This intracellular residency establishes bacterial reservoirs as sources of chronic infection. Bacteria that persist intracellularly can convert phenotypically so that upon release from aged cells, the population is able to invade new host cells more aggressively. This passage from older cells into new cells is believed to contribute to chronic, recurrent infection. Taken together, findings that ML 141 limits populations of persisting bacteria with limited cytotoxic or bactericidal activity points to the possible usefulness of targeting CDC42 to augment current therapeutic approaches for chronic, recurrent infection.

RSM series as inhibitory compounds for *Staphylococcus aureus* in endothelial cells The scope of this disclosure is to: 1) synthesize a series of ML 141 structural analogs; 2) assess these structural analogs using an invasion assay; and 3) characterize further the pharmacology of ML 141.

Experimental Section 3: Develop Analogs to Increase ML 141 Efficacy and Potency

Rationale

ML 141 demonstrates specificity for CDC42, yet compound usefulness may be limited by its solubility. The goal of this Section is to design and synthesize novel analogs with improved solubility that efficiently inhibit GTP-loading of CDC42 and *S. aureus* invasion. The modified analogs are based on the core structure ML 141 as illustrated in Scheme 0. Modifications will be made at specific locations on the core aromatics at the three and/or five positions of the pyrazoline core in an attempt to increase hydrophilicity. The aromatic pyridine heterocycles or ether and alcohol groups will increase aqueous solubility and these groups are shown as generic spheres.

Scheme 0

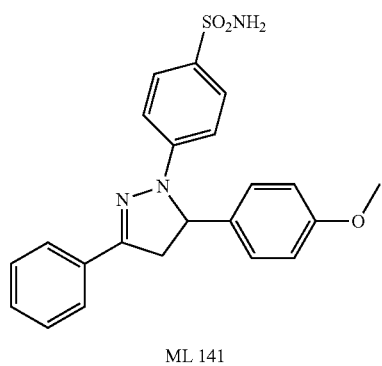

ML 141

Modified Analogs

Study 1

Addition of Small Ether or Alcohol Groups or Larger Polyethylene Glycol Appendages to Specific Locations on the Core Aromatics in an Attempt to Increase Hydrophilicity.

The proposed synthesis commences with the reaction of 4-hydroxybenzaldehyde with alkylating agents such as 2-chloroethanol, 2-(2-chloroethoxy)ethanol, 2-[2-(2-chloroethoxy)ethoxy]ethanol (R=H) or their corresponding methyl ethers (R=CH$_3$) in sodium hydroxide. The resulting ether synthesis provides a more hydrophilic benzaldehyde as shown in Scheme 1. The attachment of the small ether or alcohol groups or larger polyethylene glycol appendages to the starting acetophenone has also been proven. The mixed aldol condensation of acetophenone and 4-methoxybenzaldehyde for the synthesis of ML 141 can be adapted for the construction of proposed analogs. Following literature precedent, the reaction of substituted acetophenones with substituted benzaldehydes will prepare the required chalcones as shown in Scheme 1. These chalcones will then be condensed and cyclized with 4-hydrazinobenzenesulfonamide, which is easily prepared as the hydrochloride salt from sulfanilamide. The appendages can be extended to a longer polyethylene glycol (PEG) substituent if desired. It is well known that the addition of PEG chains to organic compounds can increase aqueous solubility without fear to biological safety. The appendages can be extended to a polyethylene glycol (PEG) substituent. Indeed, several pharmaceutical drugs have made it to market or are currently in clinical trials with hydrophilic appendages.

Scheme 1 Design of ML 141 analogs with hydrophilic substituents attached to aromatic rings.

-continued

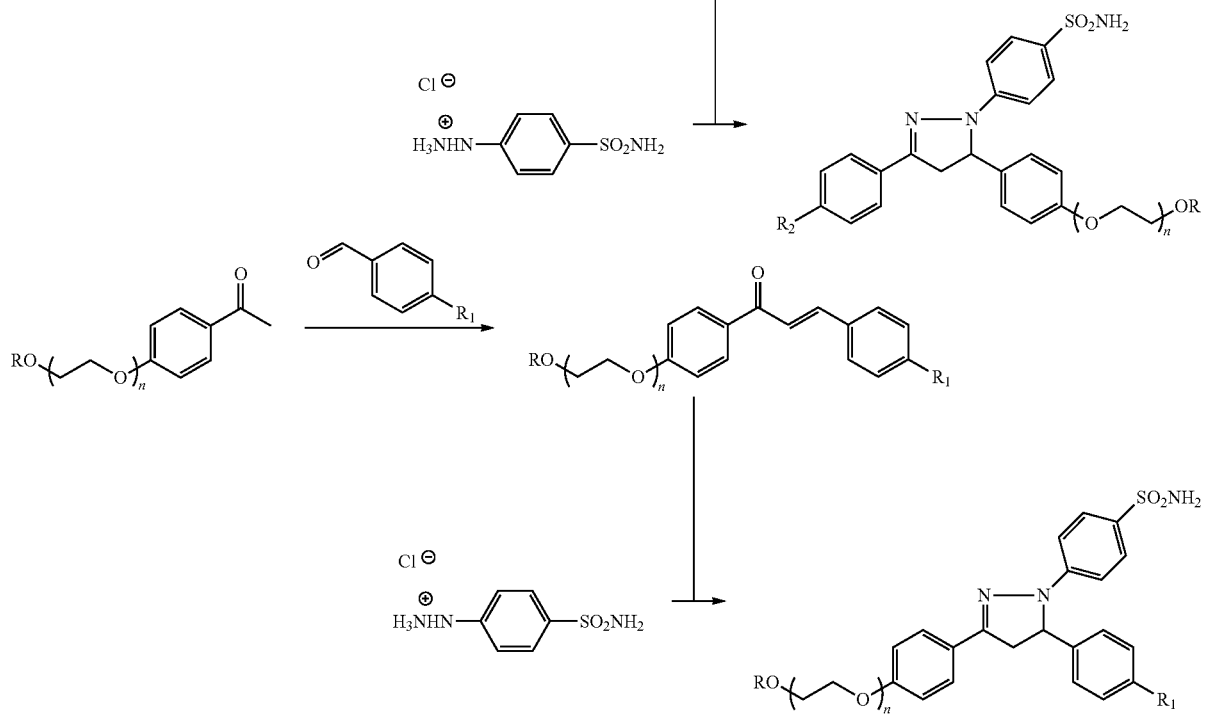

It is expected that replacement of the 4-methoxy substituent on the phenyl substituent at the five position of the pyrazoline with functionalized alkoxy substituents or addition of the functionalized alkoxy substituents to the phenyl moiety at the three position provides novel structural analogs of ML 141 with equivalent biological activity but improved solubility.

Results and Discussion

ML 141 Structural Analogs

The chemistry for the synthesis of ML 141 structural analogs is shown in Scheme 2. Hydrazine hydrochlorides are commercially available or prepared from their corresponding amines through diazotization followed by stannous chloride reduction. The prerequisite chalcones are prepared via aldol condensation from commercially available ketones with aromatic aldehydes. The general procedure is described as follows: the aldehyde (7.0 mmol) and ketone (7.0 mmol) are dissolved in ethanol (10-25 mL), the solution cooled to 0° C., and then 40% NaOH gradually added dropwise until precipitation commenced. The cold mixture is stirred until precipitation is complete and the product is then collected by vacuum filtration. The pyrazolines are synthesized as follows: the chalcone (1.0 mmol) and hydrazine hydrochloride (1.0 mmol) are dissolved in ethanol (25 mL) and a catalytic amount of sodium acetate is added (0.05 mmol). The reaction is then heated at reflux until determined complete by TLC (8-30 h). The solution is concentrated to half volume and then is cooled to produce solid product, which is then collected by vacuum filtration. If no solid is obtained, the remaining solvent is removed via rotoevaporation and the solid is taken up in ethyl acetate, washed with water, dried with sodium sulfate, filtered, and solvent evaporated to obtain crude product. Purification of crude product is achieved via recrystallization or column chromatography on silica gel.

Scheme 2: Synthesis of ML 141 structural analogs

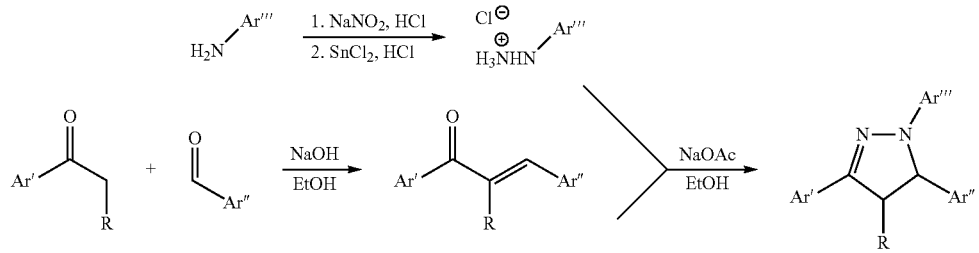

Structural analogs of ML 141 (RSM 04, 05, 06, 07, 08, 11-18), shown below in Table 2, are prepared specifically from p-sulfamylphenylhydrazine hydrochloride and the chalcones of methyl ketones and aromatic aldehydes as shown in Scheme 2. Structural analog RSM 19 is prepared from p-sulfamylphenylhydrazine hydrochloride and the chalcone of propiophenone and 4-methoxybenzaldehyde. The structural analogs are purified by standard means and characterized by IR and NMR spectroscopy.

ML 141 Structural Analogs Inhibit Host Cell Invasion

To examine whether structural analogs of ML 141 inhibit host cell invasion by *S. aureus*, HUVEC are incubated with structural analog compound (10 μM) or with an equimolar amount of ML 141 and are assayed against vehicle control treated infected samples. The majority of the structural analogs examined inhibit host cell invasion (Table 1). The following structural analogs from the RSM series showed significantly lower mean fluorescence when compared to the PEG control: RSM 04, RSM 05, RSM 06, RSM 15, and RSM 16. RSM 07, RSM 13, RSM 11, RSM 12, RSM 13 RSM 14, RSM 17, RSM 18, RSM 19, showed statistically insignificant lower mean fluorescence when compared to the PEG control.

Inhibition by RSM 5, RSM 6, RSM 7, RSM 11, RSM 12, RSM 13, RSM 19 and RSM 17, is similar to inhibition by ML 141. RSM 04, RSM 15, RSM 16, inhibited invasion more than ML 141.

TABLE 1

ML 141 structural analogs inhibit host cell invasion. Human umbilical vein endothelial cells (HUVEC) are incubated with ML 141 (10 □M), with ML 141 structural analogs (designated RSM 01-19; 10 □M), or with vehicle control polyethylene glycol (PEG, 1%), 18-20 hours prior to infection with fluorescently labeled *Staphylococcus aureus* (1 hour).

| | Internalized bacteria (% control ± SEM) | |
|---|---|---|
| | Structural analog | ML 141 |
| RSM 04 | 11 ± 1%*# | 35 ± 5%* |
| RSM 05 | 38 ± 3%*‡ | 42 ± 3%* |
| RSM 06 | 23 ± 1%*‡ | 39 ± 5%* |
| RSM 07 | 34 ± 2%*‡ | 36 ± 3%* |
| RSM 11 | 61 ± 2%*‡ | 57 ± 6%* |
| RSM 12 | 57 ± 3%*‡ | 47 ± 4%* |
| RSM 13 | 62 ± 5%*‡ | 63 ± 6%* |
| RSM 14 | 71 ± 3%*† | 51 ± 3%* |
| RSM 15 | 45 ± 1%*# | 53 ± 3%* |
| RSM 16 | 63 ± 4%*# | 89 ± 3%* |
| RSM 17 | 67 ± 8%*‡ | 66 ± 1%* |
| RSM 18 | 76 ± 7%*† | 52 ± 3%* |
| RSM 19 | 61 ± 2%*‡ | 58 ± 3%* |

Extracellular bacteria are removed using lysostaphin and gentamicin. Internalized bacteria are detected using flow cytometry
(*less than vehicle control,
†greater than ML 141,
less than ML 141, $p \leq 0.05$;
‡not different than ML 141, $p > 0.05$; n = 5/treatment).

TABLE 2

Panels A-M demonstrate the RSM series structural analogs of ML 141 and their corresponding ability to inhibit *Staphylococcus aureus* invasion of human umbilical vein endothelial cells.

Panel A: RSM 04

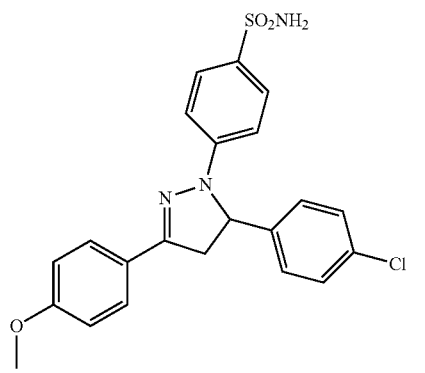

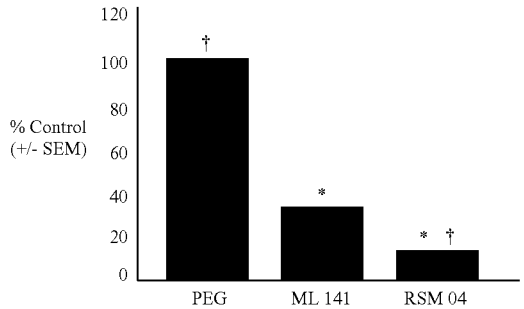

TABLE 2-continued
Panels A-M demonstrate the RSM series structural analogs of ML 141 and their corresponding ability to inhibit *Staphylococcus aureus* invasion of human umbilical vein endothelial cells.
Panel B: RSM 05
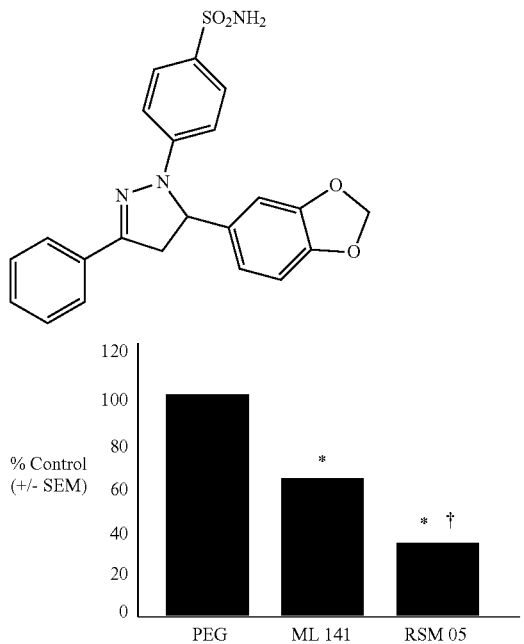
Panel C: RSM 06
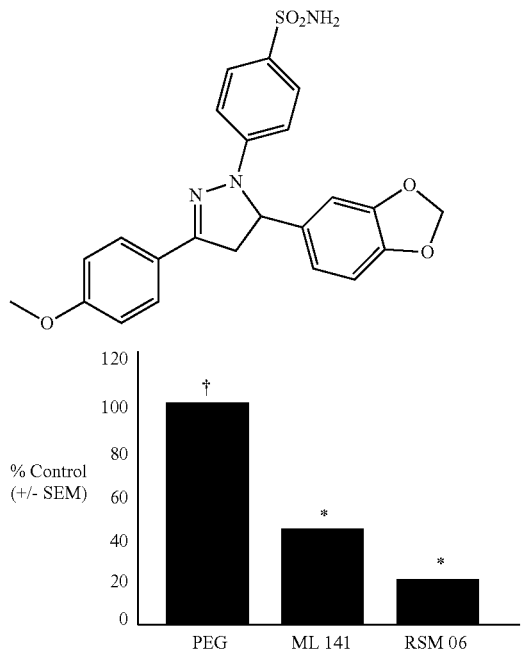

TABLE 2-continued
Panels A-M demonstrate the RSM series structural analogs of ML 141 and their corresponding ability to inhibit *Staphylococcus aureus* invasion of human umbilical vein endothelial cells.
Panel D: RSM 07
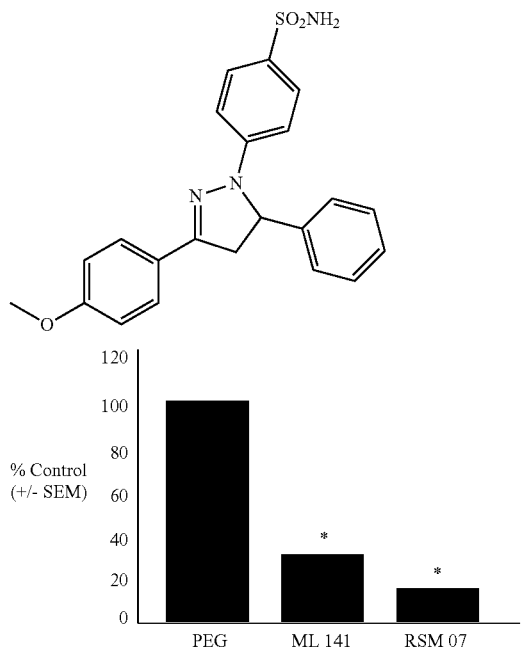
Panel E: RSM 11
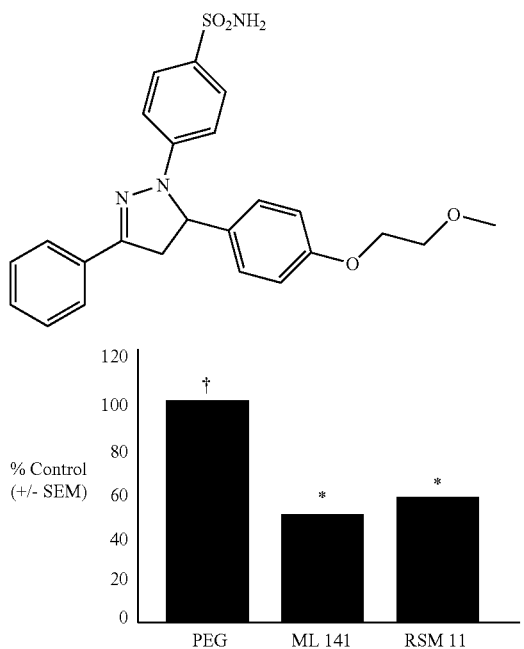

TABLE 2-continued
Panels A-M demonstrate the RSM series structural analogs of ML 141 and their corresponding ability to inhibit *Staphylococcus aureus* invasion of human umbilical vein endothelial cells.
Panel F: RSM 12
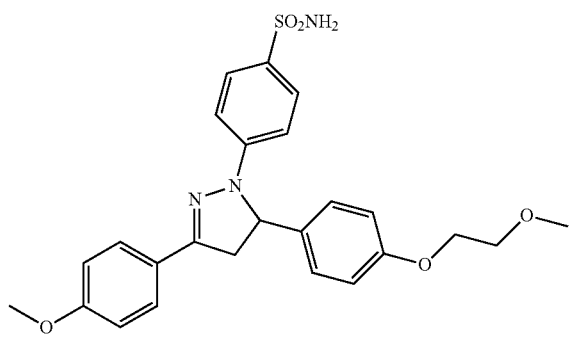
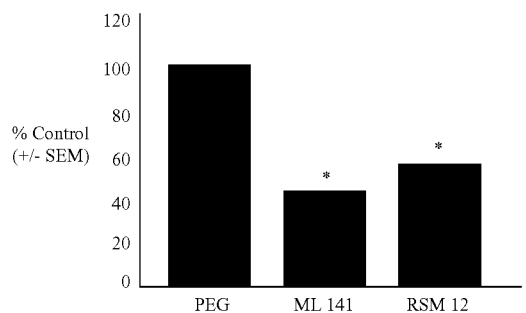
Panel G: RSM 13
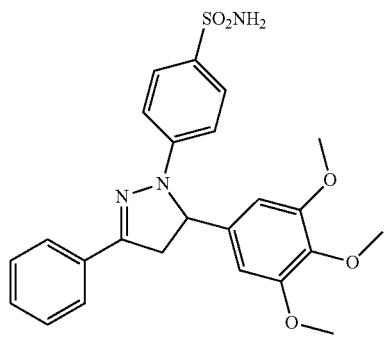
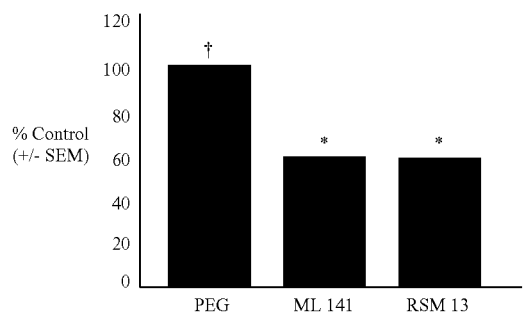

TABLE 2-continued
Panels A-M demonstrate the RSM series structural analogs of ML 141 and their corresponding ability to inhibit *Staphylococcus aureus* invasion of human umbilical vein endothelial cells.
Panel H: RSM 14
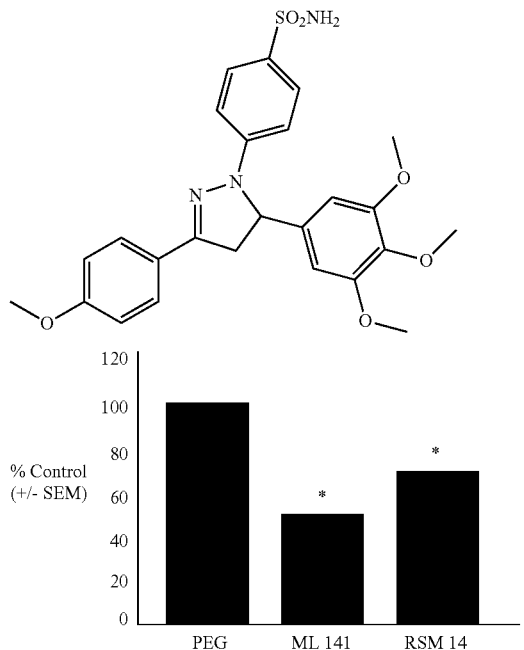
Panel I: RSM 15
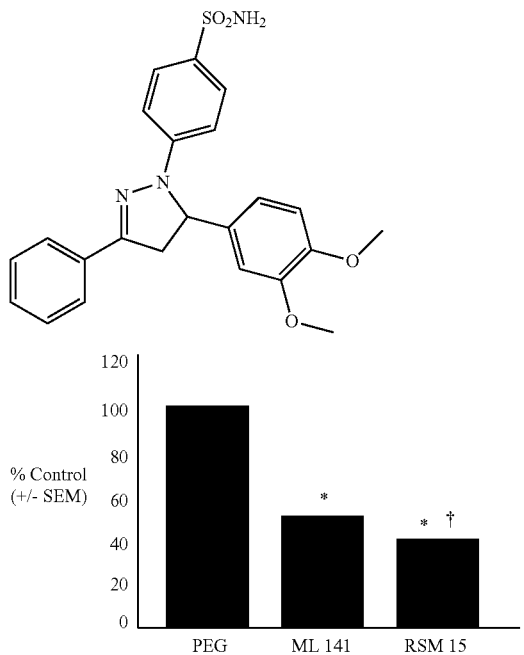

TABLE 2-continued
Panels A-M demonstrate the RSM series structural analogs of ML 141 and their corresponding ability to inhibit *Staphylococcus aureus* invasion of human umbilical vein endothelial cells.
Panel J: RSM 16
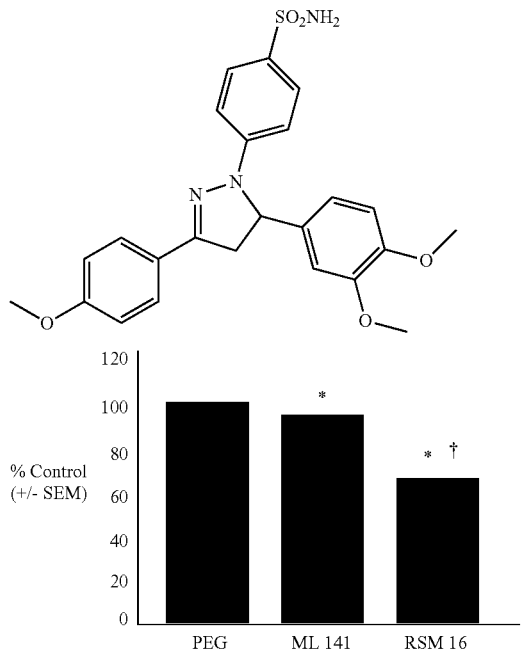
Panel K: RSM 17
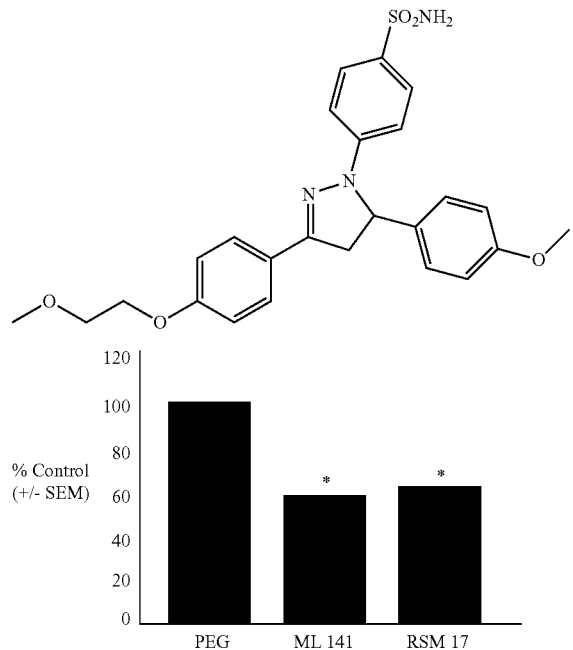

TABLE 2-continued

Panels A-M demonstrate the RSM series structural analogs of ML 141 and their corresponding ability to inhibit *Staphylococcus aureus* invasion of human umbilical vein endothelial cells.

Panel L: RSM 18

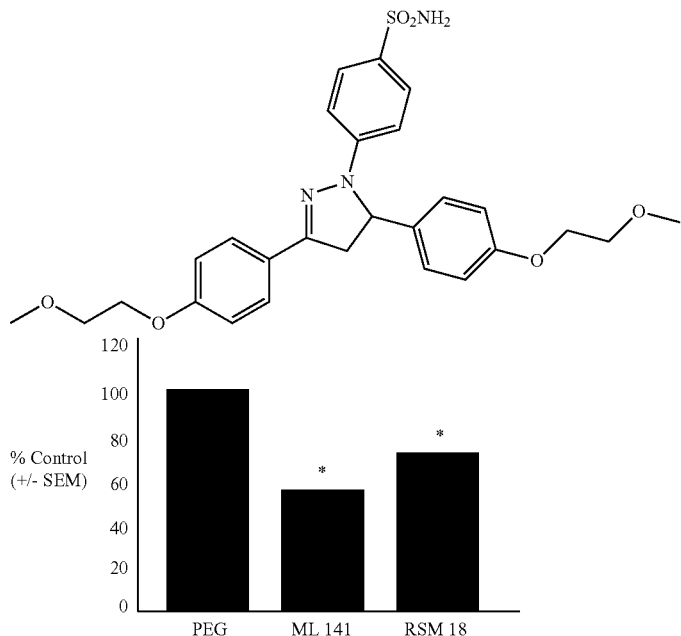

Panel M: RSM 19

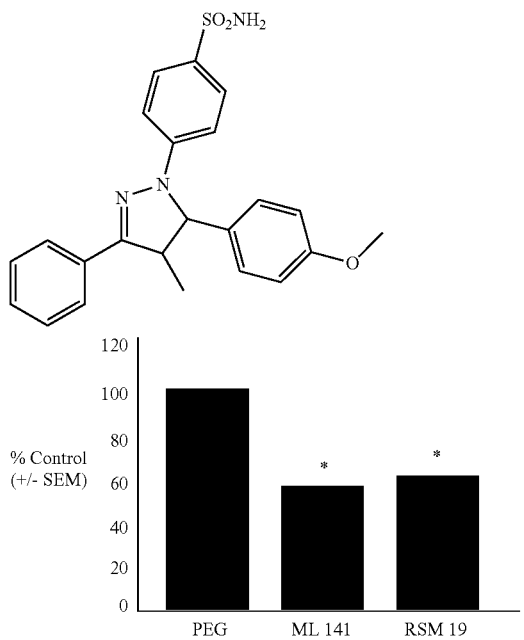

HUVEC are incubated with structural analog compound (10 μM) or with an equimolar amount of ML 141 and are assayed against vehicle control treated infected samples. The majority of the structural analogs examined inhibit host cell invasion. The following structural analogs from the RSM series showed significantly lower mean fluorescence when compared to the PEG control: RSM 04-07 and 11-19.

Inhibition by RSM 15 and of RSM 16 was more effective than ML 141.

Depolymerization of Actin Stress Fibers During Infection is Limited by ML 141

Figure 8A:
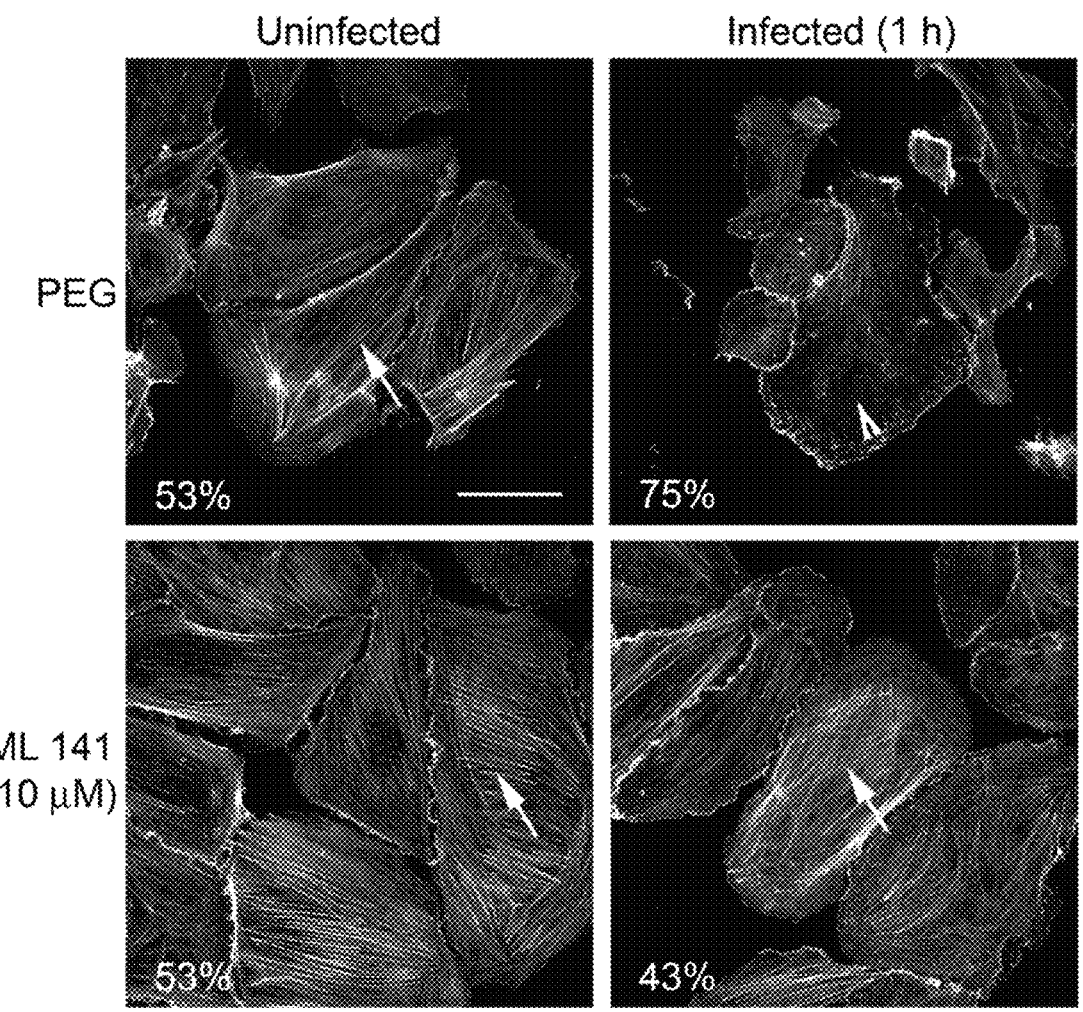
FIG. 8A is an image depicting ML 141 limiting actin stress fiber depolymerization during infection. Human umbilical vein endothelial cells (HUVEC) were incubated with ML 141 or with the vehicle control polyethylene glycol (PEG) 18-20 h prior to infection with Staphylococcus aureus (1 h). Actin was detected using Alexa Fluor 488 phalloidin. Arrows indicate intact actin stress fibers. Arrowhead indicates cell lacking actin stress fibers. 100 cells/treatment were evaluated from randomly selected fields. Data are presented as the % of cells in which actin stress fibers were not detected. Scale bar is 50 µm.
Figure 8B:
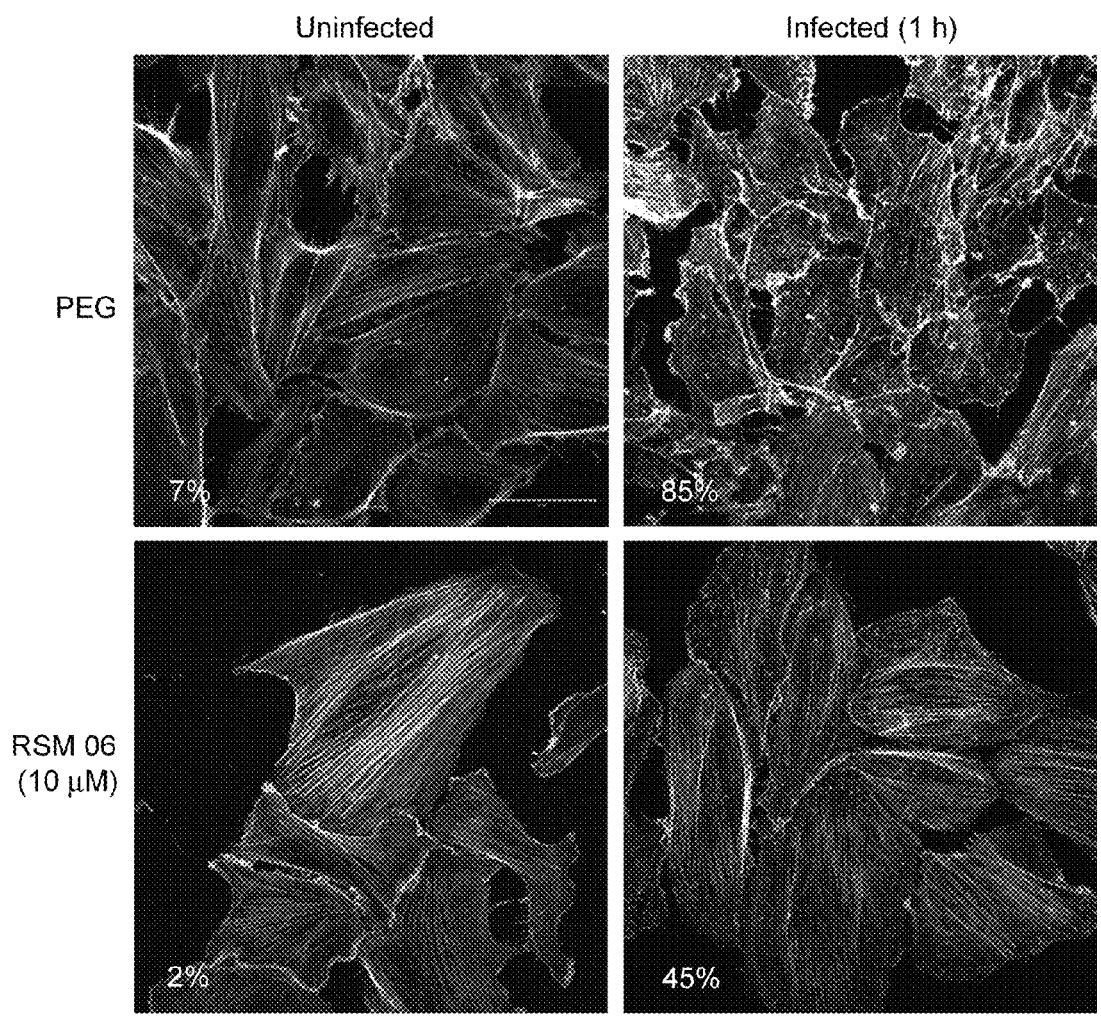
FIG. 8B is an image depicting RSM 06 limiting actin stress fiber depolymerization during infection. Human umbilical vein endothelial cells (HUVEC) were incubated with RSM 06 or with the vehicle control polyethylene glycol (PEG) 18-20 h prior to infection with Staphylococcus aureus (1 h). Actin was detected using Alexa Fluor 488 phalloidin. 200 cells/treatment were evaluated from randomly selected fields. Data are presented as the % of cells in which actin stress fibers were not detected. Scale bar is 50 µm.
Figure 8C:
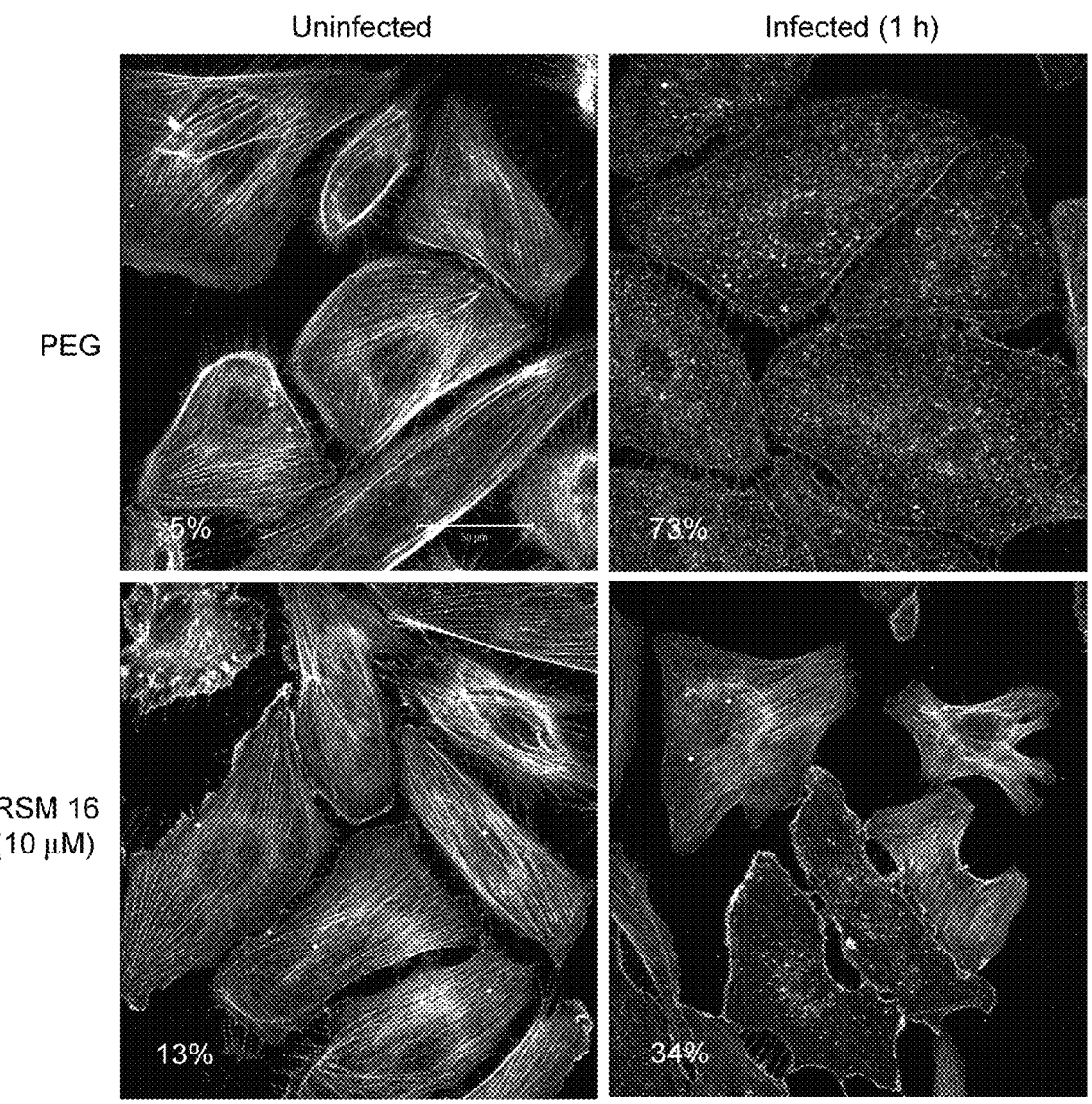
FIG. 8C is an image depicting RSM 16 limiting actin stress fiber depolymerization during infection. Human umbilical vein endothelial cells (HUVEC) were incubated with RSM 16 or with the vehicle control polyethylene glycol (PEG)

When actin stress fibers depolymerize, the actin monomers reorganize at the cell membrane to facilitate endocytic uptake. The process appears to be partially regulated by the small GTPase CDC42, indicated by the finding that in cells lacking active CDC42, depolymerization is limited as is endocytic uptake. We had found previously that host cell invasion by S. aureus stimulates the depolymerization of actin stress fibers. Inhibition of this depolymerization by LY294002, an inhibitor of phosphoinositide 3-kinase activity, was associated with decreased invasion, suggesting that the depolymerization of stress fibers and redistribution of actin at the cell membrane facilitates invasion. We therefore examined whether the specific inhibition of CDC42 using ML 141 would limit depolymerization during infection. In response to infection, stress fibers depolymerized in 75% of vehicle treated cells yet remained intact in ML 141 treated cells (FIG. 8). This finding indicates that ML 141 blunts the depolymerization of actin stress fibers during infection. The finding suggests that an underlying mechanism for ML 141 inhibition of invasion is due in part to the limited redistribution of actin required for endocytic uptake of pathogenic S. aureus. Two of the ML 141 derivatives were selected to evaluate whether either compound limited the redistribution of actin. Both RSM 06 and RSM 16 limited actin depolymerization during invasion. These findings suggest that the inhibition of invasion by RSM 6 and by RSM 16 is due in part to the limited redistribution of actin.

Implications

ML 141 and its structural analogs provide a unique tool for exploring the role of CDC42 in mediating host cell invasion. Taken together, the investigation into ML 141 and its structural analogs has the potential to provide evidence that supports future compound development for the treatment of invasive infection. Alternatively, findings may open new directions for research into the role of this small-GTPase in host immune responses. Either outcome will impact the evaluation of treatment strategies that address infection at the level of the host, elucidate cellular processes under the regulation of CDC42, and expand upon the characterization of ML 141 and its structural analogs.

NMR Data

RSM 04

$^1$H NMR (300 MHz, CDCl$_3$) δ 3.14 (dd, J=5.8 Hz, 17.0 Hz, 1H), 3.85 (s, 3H), 3.88 (dd, J=12.1 Hz, J=17.0 Hz, 1H), 4.59 (s, 2H), 5.31 (dd, J=5.8 Hz, 12.1 Hz), 6.93 (d, J=12.4 Hz, 2H), 7.03 (d, J=9.1 Hz, 2H), 7.19 (d, J=8.6 Hz, 2H), 7.31 (d, J=8.6 Hz, 2H), 7.67 (d, J=4.7 Hz, 2H), 7.69 (d, J=5.0 Hz, 2H)

RSM 05

$^1$H NMR (300 MHz, CDCl$_3$) δ 3.11 (dd, J=5.8 Hz, 17.6 Hz, 1H), 3.80 (dd, J=12.1 Hz, 17.6 Hz, 1H), 5.22 (dd, J=5.8 Hz, 12.1 Hz, 1H), 5.53 (s, 2H), 5.86 (s, 2H), 6.61 (s, 1H), 6.69 (s, 2H), 7.02 (d, J=8.3 Hz, 2H), 7.40-7.34 (m, 3H), 7.69-7.65 (m, 4H)

RSM 06

$^1$H NMR (300 MHz, CDCl$_3$) δ 3.16 (dd, J=5.8 Hz, 17.3 Hz, 1H), 3.83 (dd, J=12.4 Hz, 17.3 Hz, 1H), 3.85 (s, 3H), 5.24 (dd, J=5.8 Hz, 12.4 Hz, 1H), 5.93 (s, 2H), 6.67 (s, 1H), 6.76 (s, 2H), 6.93 (d, J=9.1 Hz, 2H), 7.07 (d, J=9.1 Hz, 2H), 7.67 (d, J=4.5 Hz, 2H), 7.69 (d, J=4.5 Hz, 2H)

RSM 07

$^1$H NMR (300 MHz, DMSO-D$_6$) δ 3.16 (dd, J=5.0 Hz, 17.6 Hz, 1H), 3.80 (s, 3H), 3.95 (dd, J=12.1 Hz, 17.6 Hz, 1H), 5.60 (dd, J=5.0 Hz, 12.1 Hz, 1H), 7.06-6.99 (m, 6H), 7.39-7.26 (m, 5H), 7.57 (d, J=9.1 Hz, 2H), 7.74 (d, J=8.8 Hz, 2H)

RSM 11

$^1$H NMR (400 MHz, CDCl$_3$) δ 3.18 (dd, J=17.2 Hz, 5.9 Hz, 1H), 3.42 (s, 3H), 3.71 (t, J=4.8 Hz, 2H), 3.86 (dd, J=17.6 Hz, 12.6 Hz, 1H), 4.06 (t, J=4.8 Hz, 2H) 4.69 (s, 2H), 5.30 (dd, J=12.1 Hz, 5.8 Hz, 1H), 6.86 (d, J=8.4 Hz, 2H), 7.07 (d, J=8.8 Hz, 2H), 7.15 (d, J=8.8 Hz, 2H), 7.35-7.43 (m, 3H), 7.67 (d, J=8.8 Hz, 2H), 7.73 (dd, J=7.6 Hz, 1.4 Hz, 2H)

RSM 12

$^1$H NMR (400 MHz, CDCl$_3$) δ 3.16 (dd, J=17.3 Hz, 5.8 Hz, 1H), 3.43 (s, 3H), 3.72 (t, J=5.0 Hz, 2H) 3.79-3.89 (m, 4H), 4.08 (t, J=4.7 Hz, 2H), 4.59 (s, 2H), 5.28 (dd, J=12.1 Hz, 5.8 Hz, 1H), 6.91 (dd, J=15.7 Hz, 8.8 Hz, 4H), 7.05 (d, J=8.8 Hz, 2H), 7.16 (d, J=8.5 Hz, 2H), 7.68 (dd, J=9.1 Hz, 4.1 Hz, 4H)

RSM 13

$^1$H NMR (300 MHz, CDCl$_3$) δ 3.23 (dd, 6.6 Hz, 17.6 Hz, 1H), 3.80 (s, 6H), 3.83 (s, 3H), 3.89 (dd, J=12.4 Hz, 17.6 Hz, 1H), 5.25 (dd, J=6.6 Hz, 12.4 Hz, 1H), 6.46 (s, 2H), 7.12 (d, J=8.8 Hz, 2H), 7.47-7.41 (m, 3H), 7.78-7.74 (m, 4H)

RSM 14

$^1$H NMR (300 MHz, CDCl$_3$) δ 3.20 (dd, J=6.6 Hz, 17.6 Hz, 1H), 3.80 (s, 6H), 3.83 (s, 3H), 3.85 (s, 3H), 3.85 (dd, J=12.1 Hz, 17.6 Hz, 1H), 5.21 (dd, J=6.6 Hz, 12.1 Hz, 1H), 6.46 (s, 2H), 6.94 (d, J=9.6 Hz, 2H), 7.09 (d, 8.8 Hz, 2H)

RSM 15

$^1$H NMR (300 MHz, DMSO-D$_6$) δ 3.19 (dd, J=5.5 Hz, 17.6 Hz, 1H), 3.69 (s, 3H) 3.72 (s, 3H), 3.94 (dd, J=12.1 Hz, 17.6 Hz, 1H), 5.54 (dd, J=5.5 Hz, 12.1 Hz, 1H), 6.69-6.67 (m, 1H), 6.88 (d, J=8.1 Hz, 1H), 6.94 (d, J=2.1 Hz, 1H), 7.09 (d, J=8.6 Hz, 2H), 7.48-7.39 (m, 3H), 7.59 (d, J=9.2 Hz, 2H), 7.79 (d, J=6.6 Hz, 2H)

RSM 16

$^1$H NMR (300 MHz, DMSO-D$_6$) δ 3.15 (dd, J=5.5 Hz, 17.6 Hz, 1H), 3.68 (s, 3H) 3.71 (s, 3H), 3.79 (s, 3H), 3.89 (dd, J=12.1 Hz, 17.6 Hz, 1H), 5.84 (dd, J=5.5 Hz, 12.1 Hz, 1H), 6.68-6.67 (m, 1H), 6.87 (d, J=8.1 Hz, 1H), 6.93 (d, J=2.1 Hz, 1H), 7.07-6.99 (m, 6H), 7.57 (d, J=9.2 Hz, 2H), 7.72 (d, J=7.8 Hz, 2H)

RSM 17

$^1$H NMR (400 MHz, CDCl$_3$) δ 3.15 (dd, J=17.6 Hz, 5.8 Hz, 1H), 3.46 (s, 3H), 3.75-3.78 (m. 5H), 3.83 (dd, J=17.2 Hz, 12.1 Hz, 1H), 4.15 (t, J=4.8 Hz, 2H), 4.60 (s, 2H), 5.28 (dd, J=12.1 Hz, 5.5 Hz, 1H), 6.85 (d, J=8.4 Hz, 2H), 6.95 (d, J=8.8 Hz, 2H), 7.05 (d, J=8.8 Hz, 2H), 7.16 (d, J=8.4 Hz, 2H), 7.67 (d, J=8.8 Hz, 4H)

RSM 18

$^1$H NMR (400 MHz, CDCl$_3$) δ 3.15 (dd, J=17.2 Hz, 5.9 Hz, 1H), 3.43 (s, 3H), 3.46 (s, 3H), 3.72 (t, J=4.8 Hz, 2H), 3.77 (t, J=4.8 Hz, 2H) 3.83 (dd, J=17.2 Hz, 12.1 Hz, 1H), 4.08 (t, J=4.8 Hz, 2H), 4.15 (t, J=4.4 Hz, 2H), 4.62 (s, 2H), 5.27 (dd, J=12.1 Hz, 5.9 Hz, 1H), 6.88 (d, J=8.8 Hz, 2H), 6.96 (d, J=8.8 Hz, 2H), 7.05 (d, J=8.8 Hz, 2H), 7.15 (d, J=8.8 Hz, 2H), 7.67 (dd, J=9.2 Hz, 2.6 Hz, 4H)

RSM 19

$^1$H NMR (400 MHz, CDCl$_3$) δ 0.84 (d, J=7.7 Hz, 3H), 3.81 (s, 3H), 3.99-4.08 (m, 1H), 4.64 (s, 2H) 5.30 (d, J=11.4 Hz, 1H) 6.87-6.90 (m, 2H), 7.08 (d, J=8.8 Hz, 2H), 7.14-7.15 (m, 2H), 7.36-7.45 (m, 3H), 7.67 (d, J=8.8 Hz, 2H), 7.77 (dd, J=8.4 Hz, 1.5 Hz, 2H)

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

We claim:

1. A method of suppressing bacterial infection comprising:
   administering ML 141 or its analogs to a patient with *Staphylococcus* infection,
   where the analogs are defined by the following structure:

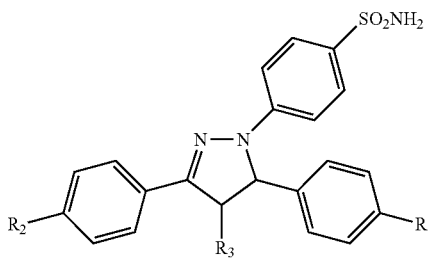

where $R_1$ is selected from the group consisting of: hydrogen, hydroxyl, halogen, methoxy, methylenedioxy (—O—$CH_2$—O—), wherein one oxygen of the methylenedioxy (—O—$CH_2$—O—) is bonded to a carbon on a phenyl ring and the other oxygen of the methylenedioxy (—O—$CH_2$—O—) is bonded to an adjacent carbon on the phenyl ring, and polyethylene glycol (—(O—$CH_2$—$CH_2$)$_n$—O-Me) wherein n is any integer;

where $R_2$ is selected from the group consisting of: hydrogen, methoxy, and polyethylene glycol (—(O—$CH_2$—$CH_2$)$_n$—O-Me) wherein n is any integer;

where $R_3$ is selected from the group consisting of: hydrogen and methyl.

2. The method of claim 1 wherein said *Staphylococcus* infection is from *Staphylococcus aureus*.

3. The method of claim 1 wherein administering includes providing ML 141 or its analogs adjacent to cells of the patient.

4. The method of claim 1 wherein administering includes testing ML 141 on cells of the patient.

5. The method of claim 1 wherein administering includes testing at least one analog on cells of the patient.

6. The method of claim 1 wherein suppressing bacterial infection includes suppressing initial bacterial infection.

7. The method of claim 1 wherein suppressing bacterial infection includes suppressing persistent bacterial infection.

8. The method of claim 7 wherein administering includes providing approximately 1 μM of ML 141.

9. The method of claim 7 wherein administering includes providing approximately 10 μM of ML 141 or its analogs.

10. The method of claim 1 wherein the patient is an animal patient.

11. The method of claim 1 wherein the patient is a human patient.

12. The method of claim 1 wherein cells of the patient include CDC42.

13. The method of claim 1, wherein $R_1$ is selected from the group consisting of methoxy, polyethylene glycol (—(O—$CH_2$—$CH_2$)$_n$—O-Me), and methylenedioxy (—O—$CH_2$—O—), where n is any integer.

14. The method of claim 1, where $R_1$ is a halogen.

15. The method of claim 14, wherein the halogen is chloride.

16. The method of claim 15, wherein ML 141 or its analogs are present in a pharmaceutically accepted solvent or delivery vehicle selected from the group consisting of polyethylene glycol (PEG), dimethyl sulfoxide, ethanol, and combinations thereof.

17. The method of claim 16, wherein the solvent or delivery vehicle is polyethylene glycol.

18. A method of suppressing bacterial infection comprising:
    administering ML 141 or its analogs to a patient infected by bacteria of the genus *Staphylococcus*,
    where the analogs are defined by the following structures:

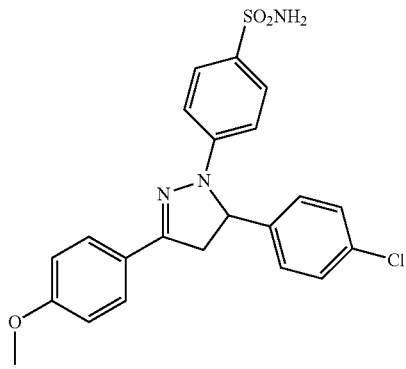

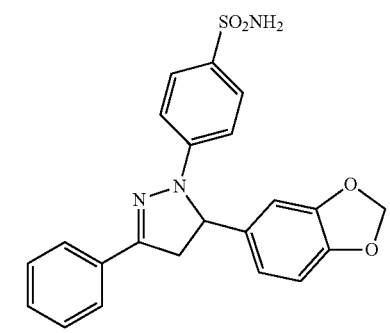

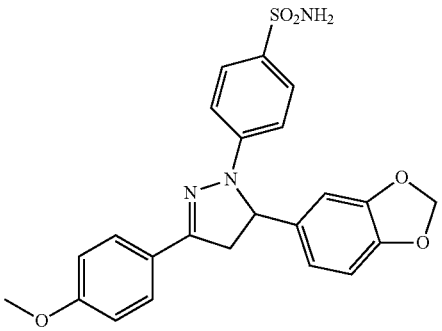

31
-continued
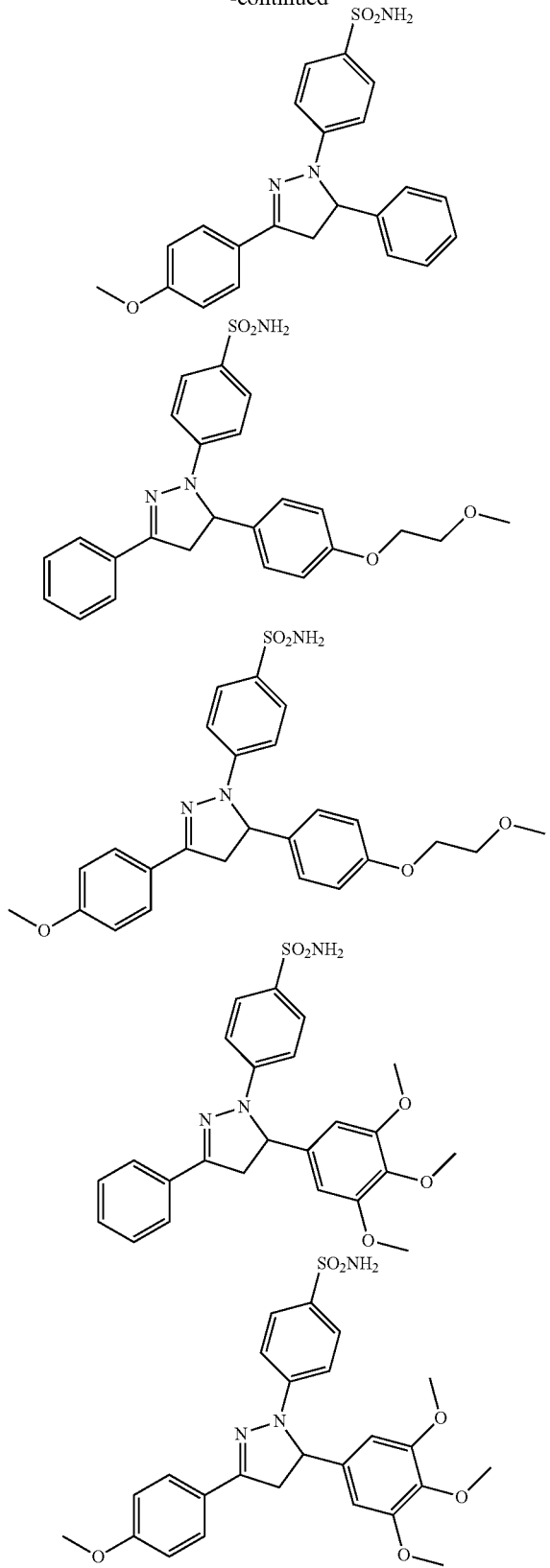
32
-continued
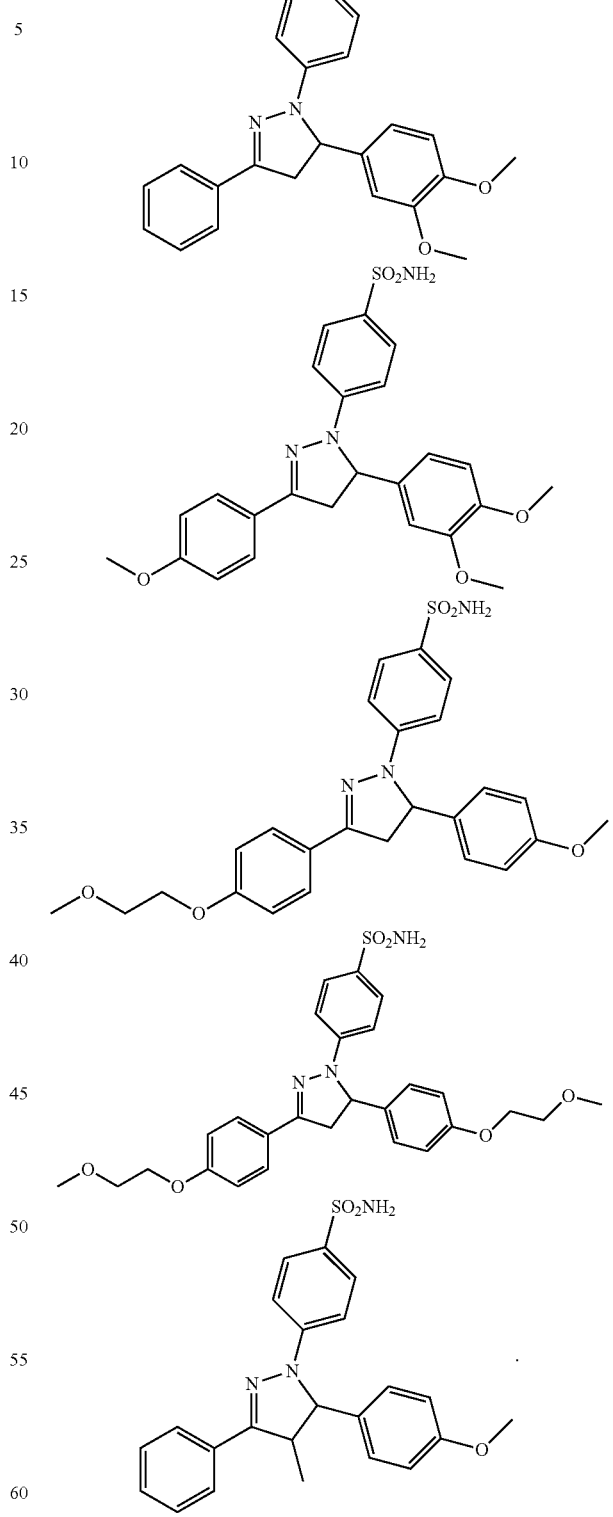
* * * * *